(12) United States Patent
Minkovska et al.

(10) Patent No.: US 12,256,907 B2
(45) Date of Patent: *Mar. 25, 2025

(54) DIGITALLY ENABLED PELVIC ASSESSMENT AND DIAGNOSIS DEVICE METHOD AND DEVICES

(71) Applicants: Stiliyana Ilieva Minkovska, London (GB); Stoyanka Spasova Minkovska, Sofia (BG)

(72) Inventors: Stiliyana Ilieva Minkovska, London (GB); Stoyanka Spasova Minkovska, Sofia (BG)

( * ) Notice: Subject to any disclaimer, the term of this patent is extended or adjusted under 35 U.S.C. 154(b) by 0 days.

This patent is subject to a terminal disclaimer.

(21) Appl. No.: 18/403,201

(22) Filed: Jan. 3, 2024

(65) Prior Publication Data
US 2024/0172935 A1 May 30, 2024

Related U.S. Application Data

(63) Continuation of application No. 18/071,601, filed on Nov. 29, 2022, now Pat. No. 11,864,738.

(51) Int. Cl.
*A61B 1/303* (2006.01)
*A61B 1/00* (2006.01)
(Continued)

(52) U.S. Cl.
CPC .......... *A61B 1/303* (2013.01); *A61B 1/00016* (2013.01); *A61B 1/0002* (2013.01);
(Continued)

(58) Field of Classification Search
CPC ... A61B 1/303; A61B 1/00016; A61B 1/0002; A61B 1/00097; A61B 1/05; A61B 1/0676; A61B 1/0684; A61B 5/01; A61B 5/4325; A61B 5/7465; A61B 2560/0462; A61B 2562/0247; A61B 2562/0271;
(Continued)

(56) References Cited

U.S. PATENT DOCUMENTS 11,864,738 B1 * 1/2024 Minkovska ........ A61B 1/00097
2011/0190579 A1 * 8/2011 Ziarno ............... A61B 1/00096
600/109

(Continued)

*Primary Examiner* — Jonathan T Kuo
(74) *Attorney, Agent, or Firm* — Edmond DeFrank

(57) ABSTRACT

The embodiments disclose a digitally enabled pelvic self-examination device including a first memory device to receive and store cervix images, a second memory device to receive and store heat detection sensor data, a first processor to convert the heat detection sensor data into superimposed overlays on the first memory device stored cervix images, a second processor to compare current stored cervix images to previously stored cervix images to determine any changes, an internet communication device coupled to a memory device and processor to receive an aggregation of data on disease prevalence and research, a third processor to generate a determination of any changes in the stored cervix images indicating any disease indications present including cervical cancer, a swab device configured to allow the user to collect a cervix tissue laboratory analysis sample, and a digitally enabled pelvic self-examination device configured to be used by user to perform a pelvic self-examination.

20 Claims, 21 Drawing Sheets

(51) Int. Cl.
   *A61B 1/05*   (2006.01)
   *A61B 1/06*   (2006.01)
   *A61B 5/00*   (2006.01)
   *A61B 5/01*   (2006.01)
   *G16H 30/40*  (2018.01)
   *H04N 23/69*  (2023.01)

(52) U.S. Cl.
   CPC ............ *A61B 1/00097* (2022.02); *A61B 1/05* (2013.01); *A61B 1/0676* (2013.01); *A61B 1/0684* (2013.01); *A61B 5/01* (2013.01); *A61B 5/4325* (2013.01); *A61B 5/7465* (2013.01); *H04N 23/69* (2023.01); *A61B 2560/0462* (2013.01); *A61B 2562/0247* (2013.01); *A61B 2562/0271* (2013.01); *A61B 2562/06* (2013.01); *G16H 30/40* (2018.01)

(58) Field of Classification Search
   CPC .. A61B 2562/06; H04N 23/69; H04N 23/555; G16H 30/40; G16H 40/67; G16H 50/20
   See application file for complete search history.

(56) References Cited

U.S. PATENT DOCUMENTS

2022/0105389 A1\* 4/2022 Lianides ............ A63B 24/0075
   2022/0370048 A1\* 11/2022 Wang ................ A61B 10/0051
   2022/0378286 A1\* 12/2022 Seeras ................ A61B 1/00071

\* cited by examiner

DIGITALLY ENABLED PELVIC ASSESSMENT AND DIAGNOSIS DEVICE METHOD AND DEVICES

This Patent Application is a Continuation and claims priority to United States Patent Application entitled: "DIGITALLY ENABLED PELVIC ASSESSMENT AND DIAGNOSIS DEVICE METHOD AND DEVICES", U.S. Ser. No. 18/071,601, filed on Nov. 29, 2022 by Stiliyana llieva Minkovska, which is incorporated herein by reference.

BACKGROUND

The speculum is a significant factor why women do not attend life-saving gynecological appointments such as the cervical cancer screenings. Cervical cancer deaths could be prevented if people attended screenings appointments regularly. A large number of women do not attend their appointment due to embarrassment of the procedure. Fear of the pain during the speculum examination prevents them from attending critical cervical screenings. More women would attend cervical cancer screenings appointments if they could perform the cervical examination themselves.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized and structural changes may be made without departing from the scope of the present invention.

General Overview

It should be noted that the descriptions that follow, for example, in terms of a digitally enabled pelvic assessment and diagnosis device method and devices is described for illustrative purposes and the underlying system can apply to any number and multiple types of a digitally enabled pelvic assessment and diagnosis device. In one embodiment of the present invention, the digitally enabled pelvic assessment and diagnosis device can be configured using a camera. The digitally enabled pelvic assessment and diagnosis device can be configured to include electronic devices and can be configured to include digital sensors using the present invention.

Many cervical cancer deaths are preventable if women attended cervical cancer screening regularly. This means numerous eligible individuals (aged between 24-65 years) are not screened every year. For example, many lesbian or bisexual women never have had a cervical cancer screening, while many women do not attend their cervical cancer screening appointments due to embarrassment of the procedure. In other cases, many women fear the pain caused during a cervical examination and thus, don't attend their cervical prevention screening. In other cases, women fell nervous when they attended their cervical screening.

There is a cost of not attending appointments and the cost of Cervical Cancer Screening Programs with many governmental health agencies. This is because these agencies are required to cover cervical diseases that could have been prevented. The annual cost of preventable cervical diseases is billions of dollars. The cost is due in part to hundreds and thousands of doctors, nurses and healthcare assistants losing time with missed appointments. Other costs include the money spent on medical treatments that could have been prevented if the cervical disease was caught early with cervical cancer screening.

Figure 1:
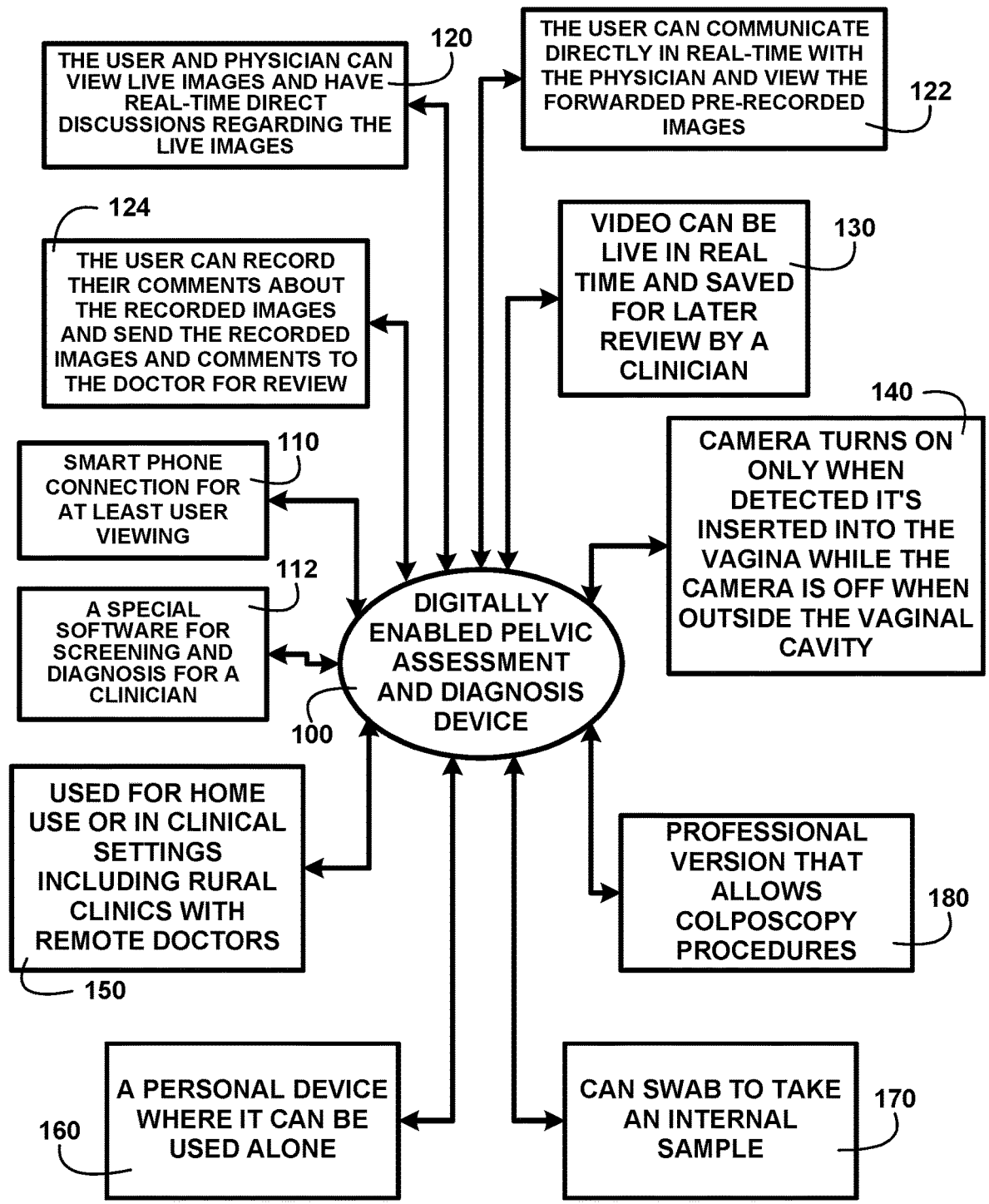
FIG. 1 shows a block diagram of an overview of a digitally enabled pelvic assessment and diagnosis device features of one embodiment.

FIG. 1 shows a block diagram of an overview of a digitally enabled pelvic assessment and diagnosis device with certain features of one embodiment. FIG. 1 shows a digitally enabled pelvic assessment and diagnosis device 100. The digitally enabled pelvic assessment and diagnosis device 100 includes elements and features to allow a user to perform self-examination in private and communicate the self-examination results to the user's physician or clinician. The elements include a mobile device, such as a smart phone, with a connection for at least user viewing 110. The results can be accessed via the smart phone by the user. In another embodiment, a special software is included for screening and diagnosis for a clinician 112 to access the results. In one embodiment, the user and physician can view live images and have real-time direct discussions regarding the live images 120. In another embodiment, the user can communicate directly in real-time with the physician and view the forwarded pre-recorded images 122. In yet another embodiment, the user can record their comments about the recorded images and send the recorded images and comments to the doctor for review 124. The video images can be live in real time and saved forever for later review by a clinician 130. In one embodiment, the digitally enabled pelvic assessment and diagnosis device 100 camera turns on only when the device 100 detects it's inserted into vagina. In contrast, when the device is outside the vaginal cavity 140, the camera turns off. This prevents users from exposing their external anatomical images when the device is not visually examining internal organs. The digitally enabled pelvic assessment and diagnosis device 100 may be used for home use or in clinical settings, including rural clinics with remote doctors 150.

In another embodiment, the digitally enabled pelvic assessment and diagnosis device 100 includes an internal gimbal connected to the camera lens and an articulation motor. In this embodiment, the end user and a remote user, such as a physician and/or specialist, are connected to the digitally enabled pelvic assessment and diagnosis device 100 via their own respective mobile software application. This allows the remote physician to access the internal gimbal and remotely articulate and manipulate the camera lens as the user holds the device 100 steady. The ability to remotely control the inserted digitally enabled pelvic assessment and diagnosis device 100 allows the remote physician to access desired camera field of visions for a more thorough examination.

In one embodiment, the digitally enabled pelvic assessment and diagnosis device 100 is a personal device that it can be used alone 160. In addition, the digitally enabled pelvic assessment and diagnosis device 100 can having swabbing capabilities to allow it to take an internal swab sample 170 from internal organs. In another embodiment, the digitally enabled pelvic assessment and diagnosis device 100 is a professional device that allows colposcopy procedures 180 and other internal organ visual assessment capabilities, for example for use as a sigmoidoscopy for anal and rectal digital visual examinations to evaluate the lower part of the large intestine, colon and anus. These digital visual examinations include examinations of the colon and the anus for anal fissures, polyps, hemorrhoids and other abnormalities of the anus and lower colon.

The following are steps in one example embodiment for the use of the digitally enabled pelvic assessment and diagnosis device 100. In this example embodiment, the steps include: Step 1 attend appointment (pap smear test or pelvic exam); Step 2 collect digitally enabled pelvic assessment and diagnosis device from clinician's room and prepare for self-exam; Step 3 self-apply the digitally enabled pelvic assessment and diagnosis device 100 for collecting visual data; Step 4 perform self-swab with a self-swab device kit for cervical cytology collection; Step 5 return kit to clinician for brief consultation. Benefits include clinicians do not need to leave their desk and user patients go behind the curtains or in a separate room to perform the self-examination of one embodiment.

DETAILED DESCRIPTION

Figure 2:
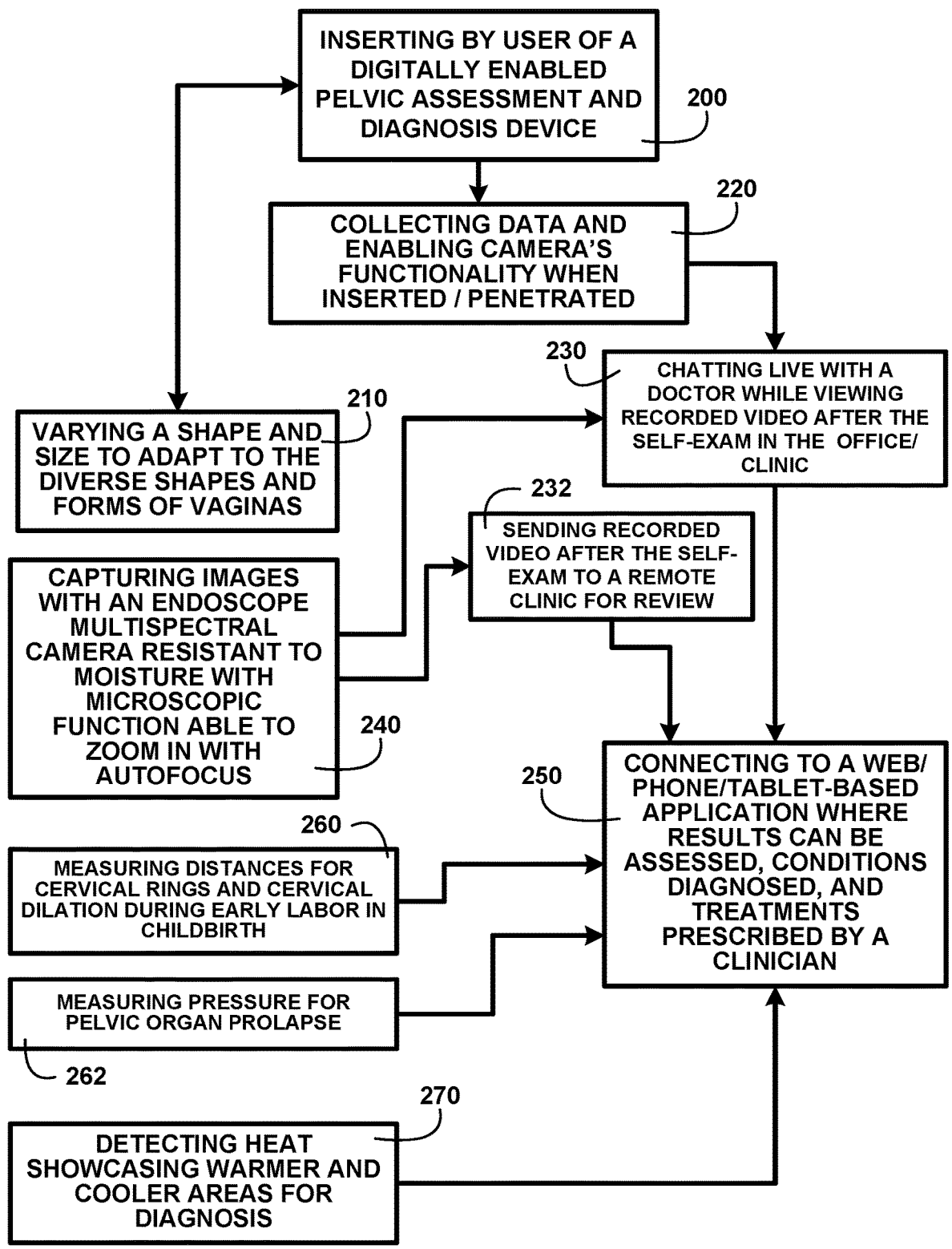
FIG. 2 shows a block diagram of an overview flow chart of a digitally enabled pelvic assessment and diagnosis device of one embodiment.

FIG. 2 shows a block diagram of an overview flow chart of a digitally enabled pelvic assessment and diagnosis device of one embodiment. FIG. 2A shows inserting by a user of a digitally enabled pelvic assessment and diagnosis device 200. The digitally enabled pelvic assessment and diagnosis device 100 of FIG. 1 is provided with varying shapes and sizes to adapt to the diverse shapes and forms of different vaginas 210 of women. In one embodiment, the device 100 can be used for collecting data and enabling the camera's functionality when inserted/penetrated 220. In another embodiment, the device 100 can be used for chatting live with a doctor while viewing recorded video after the self-exam in the office/clinic 230. In another embodiment, the device can be used for sending recorded video after the self-exam to a remote clinic for review 232.

In this embodiment, the device 100 is used for capturing images with an endoscope multispectral camera resistant to moisture with microscopic function able to zoom in with autofocus 240; connecting to a user web/smart phone/tablet-based application where results can be assessed, conditions diagnosed, and treatments prescribed by a clinician 250; measuring distances for cervical rings and cervical dilation during early labor in childbirth 260; measuring pressure for pelvic organ prolapse 262; and detecting heat showcasing warmer and cooler areas for diagnosis 270. Temperature differences between warmer and cooler areas in the vagina interior and cervix may provide detection of possible cervical malignant and premalignant lesions. Studies have shown that there are significant temperature differences between invasive cervical cancer and benign lesions or healthy cervix.

Typically, a colposcopic exam is used to detect lesions. While a colposcopy does not go inside the vagina, it is used to view through an opening made with a speculum. The colposcopy shines a light through the speculum vaginal opening to view the cervix. It would be extremely awkward for a woman to perform a colposcopic self-examination. For example, it is awkward for one hand to hold the speculum, and the other hand to hold the colposcopy. This would make it virtually impossible to view through the colposcopy binocular lenses to look for any lesions, thereby making self-examination impractical.

In contrast to the digitally enabled pelvic assessment and diagnosis device 100 of FIG. 1, which is inserted into the vagina and is in close proximity to the cervix. The close proximity is illuminated with a light to allow images to be taken with the endoscope multispectral camera with microscopic function. In addition, the heat detection sensors also in close proximity for collecting data on the temperatures of the tissues being image captured. A button near the distal end of the digitally enabled pelvic assessment and diagnosis device 100 of FIG. 1 can be pressed with a finger or thumb of the same hand holding the device. The button includes a zoom in-out toggle switch with which the user can adjust the image viewed on the user smart phone before taking a photograph or during a 3D scanning video. The camera includes a high-definition (HD) camera with autofocus capabilities. The detected temperatures are color coded and superimposed on the images being captured. This enables the user of the digitally enabled pelvic assessment and diagnosis device 100 of FIG. 1 and a remote clinician to simultaneously view the images and data. In one embodiment sound/sonar/ultrasound capabilities are integrated into the digitally enabled pelvic assessment and diagnosis device 100 of FIG. 1. In another embodiment a laser ablation tool at the inserted end or either side of the device—can see with the camera where to perform internal vagina laser treatment to polyps, cysts, etc. In yet another embodiment a pathogen sensor is coupled to the digitally enabled pelvic assessment and diagnosis device 100 of FIG. 1 that can immediately detect the existence of viruses, bacteria and certain infectious diseases and yeast infections when probing. Another embodiment includes sensors that can detect inflammation and possible infections using machine learning for comparisons with stored known inflammation and possible infections. One embodiment includes a single-photon avalanche diode (SPAD) is coupled to the digitally enabled pelvic assessment and diagnosis device 100 of FIG. 1, which allows the camera to capture high amounts of detail with only one-tenth of the brightness required by other image sensors. SPAD sensors work by amplifying a single photon that enters the sensor's pixels into large amounts of electrical energy pulses, which then allows the camera to see objects in areas with small amounts of light. In one embodiment an electronic sensor is configured for generating multiple electrons from a single photon gives greater sensitivity during image capture. Combined with 3.2 million pixels, the sensor provides the camera with extreme image clarity. In another embodiment Forensic Wide Dynamic Range (WDR) sensors: when images are underexposed or overexposed it can be impossible to identify objects. WDR solves the issue by applying multiple exposure levels, contrast enhancement, and advanced algorithms that lower noise and increase the image signal.

The user and clinician can have a pre-diagnosis on the findings where it is warranted to allow the clinician to suggest a biopsy of suspected possible cervical malignant and premalignant lesions. This allows the digitally enabled pelvic assessment and diagnosis device 100 of FIG. 1 to provide faster, more convenient, less intrusive and complete data that informs the user and clinician of possible follow-up procedures.

In one embodiment, the digitally enabled pelvic assessment and diagnosis device 100 is a portable instrument which a woman can insert into her vagina with privacy and comfort. The digitally enabled pelvic assessment and diagnosis device 100 allows the user to view and record video images of the interior of her vagina and cervix. The images are viewable on a user mobile device, such as a smart phone, tablet, computer and other mobile digital devices. Recording the images on memory in the user smart phone, tablet, computer and other mobile digital devices enable the user to share the images in real time and with remote clinicians at a later time.

In one embodiment, the user can communicate directly in real-time with the physician for forwarding the recorded images. In another embodiment, the user can record their comments about the recorded images and send the recorded images and comments to the physician for review. In yet another embodiment, the user and physician can view live images together and have real-time direct discussions regarding the live images. In this instance, the physician may direct the user to adjust the camera to a certain location or adjust the zoom setting for a closer view. In another embodiment, the digitally enabled pelvic assessment and diagnosis device 100 includes an internal gimbal connected to the camera lens and an articulation motor. In this embodiment, both the end user and a remote user, such as a physician or nurse, are connected to the digitally enabled pelvic assessment and diagnosis device via their own respective mobile application. This allows the remote user to access the internal gimbal via remote software remote controls on their mobile application to remotely articulate and manipulate the camera lens as the end user holds the device 100 steady. This allows an expert remote user to remotely control the inserted digitally enabled pelvic assessment and diagnosis device. In this case, the expert remote user can access desired camera field of visions for a more thorough examination.

In another embodiment, the digitally enabled pelvic assessment and diagnosis device 100 is reusable. The device includes at least one rechargeable battery and is equipped with a USB recharging port. A medical grade silicon jacket allows the device to be sterilized with a wipe. In addition, a biodegradable prophylactic deice, such as a condom, can be used to cover the device prior to insertion to further prevent transfer of infectious diseases.

The digitally enabled pelvic assessment and diagnosis device 100 can be used for visual, sensor, electronic detection devices, heat detection, 3D scanning and distance measurements with other interior of cavities or tubes of the body by visual or photographical inspection. In another embodiment, the camera lens includes multiple lens to accomplish 3D scanning and 360 degree camera views. Multiple camera lenses allow more detailed views of the internal areas of the vaginal canal and internal organs. The digitally enabled pelvic assessment and diagnosis device 100 is a medical instrument for self-examination personal use for example at home or in a medical office yet in private in a separate room or behind curtains.

The digitally enabled pelvic assessment and diagnosis device 100 also can include an insertable swab instrument to obtain samples from the interior tissues. The tissue swabs can be sent to a clinician for laboratory analysis. The camera can capture where the swab is taken from within the interior tissues to provide additional diagnostic data for analysis. In one embodiment, both the end user and a remote expert, such as a physician and/or specialist, are connected to the digitally enabled pelvic assessment and diagnosis device via their own respective mobile application. This allows the remote expert to instruct the end user on how and where to manipulate the device to take a swab from a desired area. In yet another embodiment, the swab can also be taken by the expert remotely with a digitally enabled internal swabber connected to an articulation motor. In this embodiment, both the end user and the remote physician and/or specialist are connected to the digitally enabled pelvic assessment and diagnosis device via their own respective mobile application. This allows the remote expert to articulate the remote swabber so the expert can take a swab from a desired area remotely using software remote controls on the software application to control the device 100.

The ability to self-exam provides a user with a comfortable, non-intrusive, comprehensive manner to perform for example vaginal screenings for in one example cervical cancer more frequently, in the convenience of their residence. This convenience makes monitoring the vaginal area, vaginal canal and areas near and proximate to the vaginal area more effective for monitoring reproductive health issues in a timely manner for prevention and early detection. Early detection conditions will lead to early treatment and less risk of death caused by treatable diseases.

Figure 3:
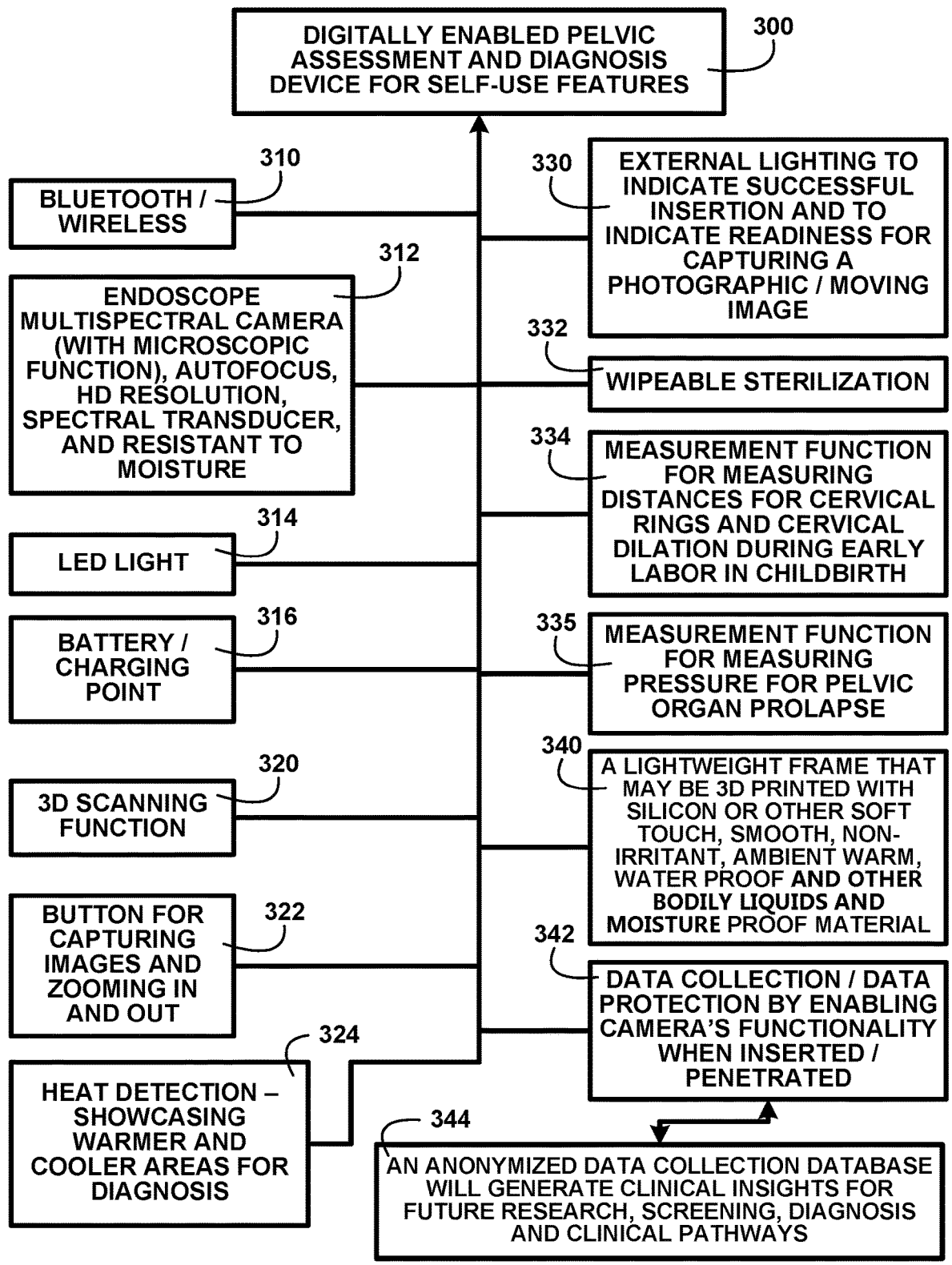
FIG. 3 shows a block diagram of an overview of a digitally enabled pelvic assessment and diagnosis device elements and features of one embodiment.

Digitally Enabled Pelvic Assessment and Diagnosis Device Elements and Features:

FIG. 3 shows a block diagram of an overview of a digitally enabled pelvic assessment and diagnosis device elements and features of one embodiment. FIG. 3 shows digitally enabled pelvic assessment and diagnosis device for self-use features 300. The features include Bluetooth/wireless 310 communication devices. Other features include an endoscope multispectral camera (with microscopic function), autofocus, high definition (HD) resolution, spectral transducer, three-dimensional (3D) camera lens arrangements, 360 degree camera lens arrangements, a moisture resistant housing 312 and suitable lighting, such as infrared capabilities, LED lighting 314 or other suitable lighting instruments to allow camera illumination of and full viewing of internal structures. Also included is a battery/charging point 316 to recharge the rechargeable batteries.

In another embodiment, an augmented reality feature can be included in the mobile application to allow other images and videos of stored similar vaginal areas to be overlayed and superimposed on the current images and videos being displayed. This overlaying and superimposing of other stored normal or abnormal images and videos allows a user to visually compare their current images and video of their vaginal area to the stored normal and abnormal images and videos. In yet another embodiment, an artificial intelligence comparison engine can be incorporated in the mobile application. The artificial intelligence comparison engine can use machine learning to compare the other stored normal or abnormal images and videos to the current images and video of the vaginal area during examination to detect abnormal and normal aspects of the vaginal area being examined. Also, a virtual reality application can be used on the mobile application to train a user on how to use and manipulate the device 100.

In another embodiment, a 3D scanning function 320 is included to capture 3D images and determine distances and depths of internal structures. A button for capturing images and zooming in and out 322 can be used while the digitally enabled pelvic assessment and diagnosis device 100 of FIG. 1 is inserted. Heat detection can be included to showcase warmer and cooler areas for diagnosis 324. External lighting can be included to indicate successful insertion and to indicate readiness for capturing a photographic/moving image 330.

In another embodiment, wipeable sterilization 332 can be included to prevent transfer of infectious microorganisms to another user. A measurement function can also be included for measuring distances for cervical rings and cervical dilation during early labor in childbirth 334. A measurement function can also be included for measuring pressure for pelvic organ prolapse 335. A lightweight frame that may be 3D printed with silicon or other soft touch, smooth, non-irritant, ambient warm, waterproof and other bodily liquids and moisture material 340 can be included. Data collection/data protection can be accomplished by enabling camera's functionality when inserted/penetrated 342. Data collection stored in an anonymized data collection database can generate clinical insights for future research, screening, diagnosis and clinical pathways 344 of one embodiment.

Figure 4:
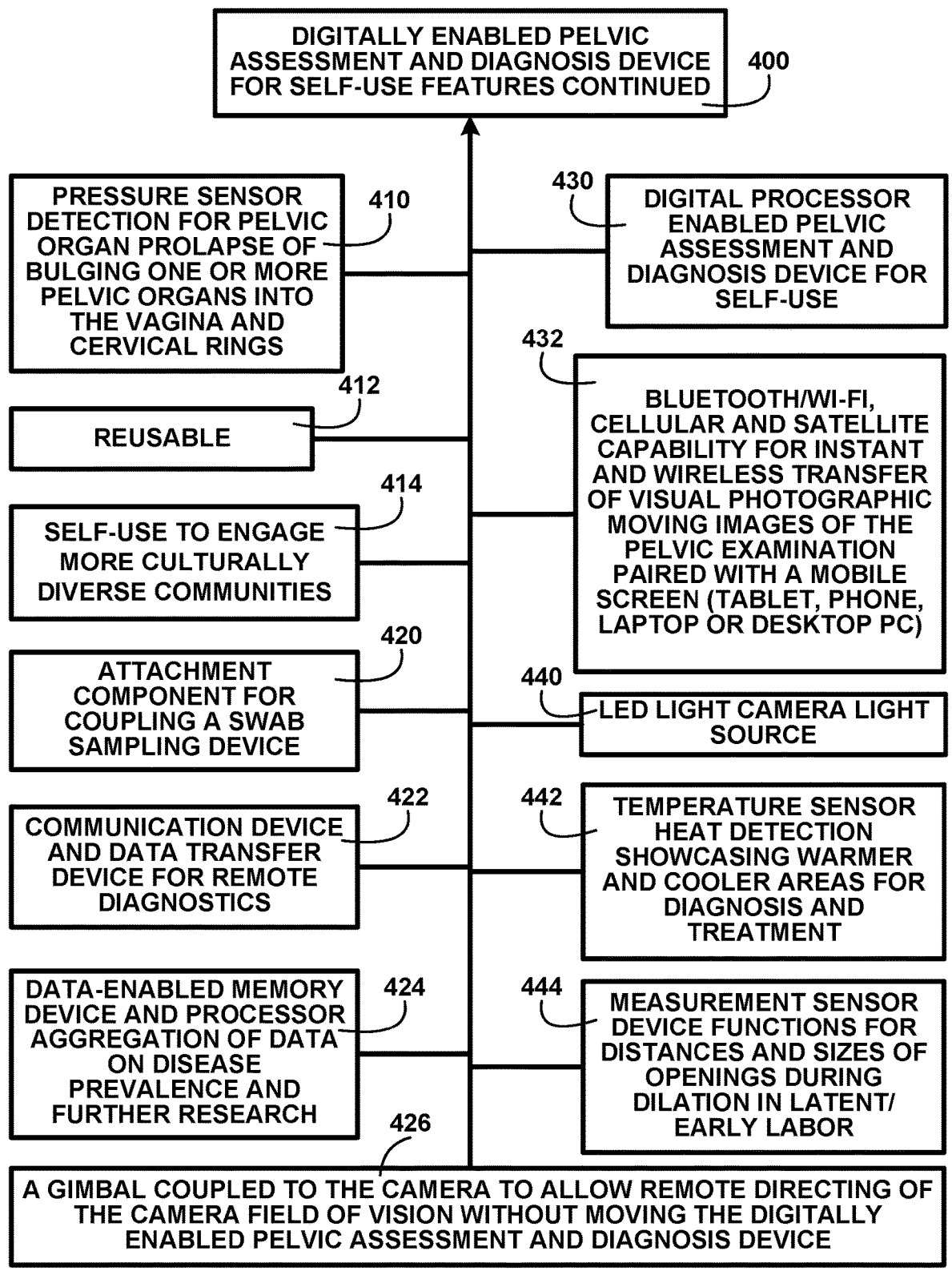
FIG. 4 shows a block diagram of an overview of a digitally enabled pelvic assessment and diagnosis device self-use features of one embodiment.

Digitally Enabled Pelvic Assessment and Diagnosis Device Self-Use Features:

FIG. 4 shows a block diagram of an overview of a digitally enabled pelvic assessment and diagnosis device self-use features of one embodiment. FIG. 4 shows digitally enabled pelvic assessment and diagnosis device for self-use features continued 400. The self-use features further include pressure sensor detection for pelvic organ prolapse of bulging one or more pelvic organs into the vagina and cervical rings 410. Self-use features include allowing the digitally enabled pelvic assessment and diagnosis device 100 of FIG. 1 to be reusable 412. The digitally enabled pelvic assessment and diagnosis device 100 of FIG. 1 is configured for self-use to engage more culturally diverse communities 414. An attachment component is included for coupling a swab sampling device 420.

A communication device and data transfer device is used for remote diagnostics 422. A data-enabled memory device and processor is used for aggregation of data on disease prevalence and further research 424. A gimbal coupled to the camera to allow remote directing of the camera field of vision without moving the digitally enabled pelvic assessment and diagnosis device 426. A digital processor is also enabled with the pelvic assessment and diagnosis device for self-use 430. Communication devices are used with connectivity with devices including Bluetooth, WIFI, cellular, and satellite capability for instant and wireless transfer of visual photographic and moving images of the pelvic examination paired with a mobile screen (tablet, phone, laptop or desktop pc) 432.

If communication connectivity is not as readily available in rural areas, satellite connectivity communication devices would be available for user communication with a remote physician or clinician. The sharing of digitally enabled pelvic assessment and diagnosis device 100 of FIG. 1 images and data can be transmitted via a satellite communication link and voice and real-time discussions between the user and physician can be conducted. Recorded images photographic and video with other data collected can be sent overnight and viewed at a convenient time between the user and physician.

In one embodiment, a LED light camera light source 440 that can be remotely turned on and off, dimmed and articulated and controlled via the mobile application is included. A temperature sensor heat detection showcasing warmer and cooler areas for diagnosis and treatment 442 can also be included. A measurement sensor device is included in one embodiment with remote controls on the mobile application to allow functions for distances and sizes of openings during dilation in latent/early labor 444.

The data-enabled memory device and processor can be used for aggregation of data on disease prevalence and further research 424 data and information and is viewable to the user on a user smart phone, tablet, computer and other mobile digital devices. This allows the user to become educated on the possible vaginal conditions using the digitally enabled pelvic assessment and diagnosis device 100 of FIG. 1 through the video and images taken.

The necessity of frequent screening for cervical cancer is better understood as the user learns more on the disease prevalence. The research data and information will equip the user with knowledge to recognize and determine when the images and data collected with the digitally enabled pelvic assessment and diagnosis device 100 of FIG. 1 possibly show indications the user should discuss with their physician. The user will also learn of advances in treatments for cervical cancer particularly when detected early. This will provide motivation for the user to perform self-examination with the digitally enabled pelvic assessment and diagnosis device 100 of FIG. 1 for early detection.

Additionally, when discussing the images and data collected with their physician, the user will be able to understand more readily the physician's comments. The aggregation of data on disease prevalence and further research 424 data and information is updated continuously and recorded on the user smart phone, tablet, computer and other mobile digital devices. This is especially beneficial to users in remote and rural areas where local information may not be available or very outdated. The knowledge availability may reduce any overwhelming fear the user may otherwise experience if they do not understand what they are viewing in the images.

For example, if the user sees a lesion on the cervix, the lesion could be a cervical malignant and premalignant lesion. The lesion could also be a benign lesion or healthy cervix tissue. Without adequate knowledge the user could leap to mistaken conclusions and become distraught. The heat detection information when understood could show the temperature of the tissues is not indicating a significant temperature difference normally seen between invasive cervical cancer and benign lesions or healthy cervix. A communication device coupled to the first, second, and third memory devices configured to transmit pelvic images and videos and stored data to a user's electronic medical records. Thus, the digitally enabled pelvic assessment and diagnosis device 100 of FIG. 1 can provide images and data in a more convenient and comfortable manner. It also provides a knowledge resource in a convenient manner and information to comfort the user's emotional state and mental wellbeing regarding the health issues involved of one embodiment.

Figure 5:
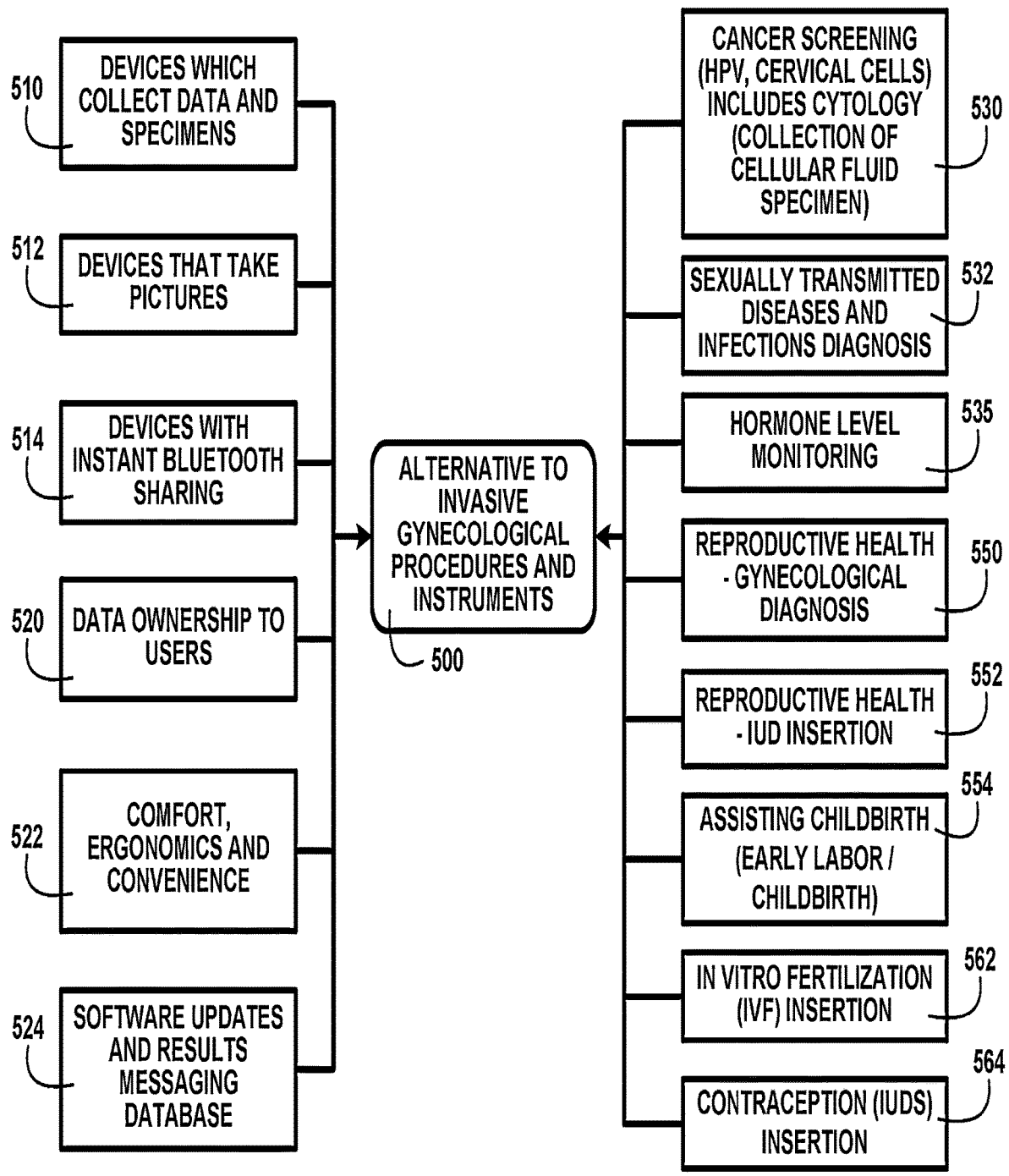
FIG. 5 shows a block diagram of an overview of digitally enabled pelvic self-examination device features of one embodiment.

Digitally Enabled Pelvic Self-Examination Device Features:

FIG. 5 shows a block diagram of an overview of digitally enabled pelvic self-examination device features of one embodiment. FIG. 5 shows the digitally enabled pelvic assessment and diagnosis device 100 of FIG. 1 as an alternative to invasive gynecological procedures and instruments 500. The digitally enabled pelvic assessment and diagnosis device 100 of FIG. 1 includes devices that collect data and specimens 510, devices that take pictures 512, devices with instant Bluetooth sharing 514, data ownership to users 520, comfort, ergonomics and convenience 522 for the user and software updates and a results messaging database 524. The digitally enabled pelvic assessment and diagnosis device 100 of FIG. 1 can be used for cancer screening (HPV, cervical cells), which includes cytology (collection of cellular fluid specimen) 530 with swab sample collection. The digitally enabled pelvic assessment and diagnosis device 100 of FIG. 1 can be used to detect sexually transmitted diseases and infections diagnosis 532, hormone level monitoring 535, reproductive health, such as gynecological diagnosis 550, reproductive health, such as IUD insertion 552, assisting childbirth (early labor/childbirth) 554 procedures, in vitro fertilization (IVF) 562 procedures and contraception (IUDs) 564 procedures of one embodiment.

Figure 6:
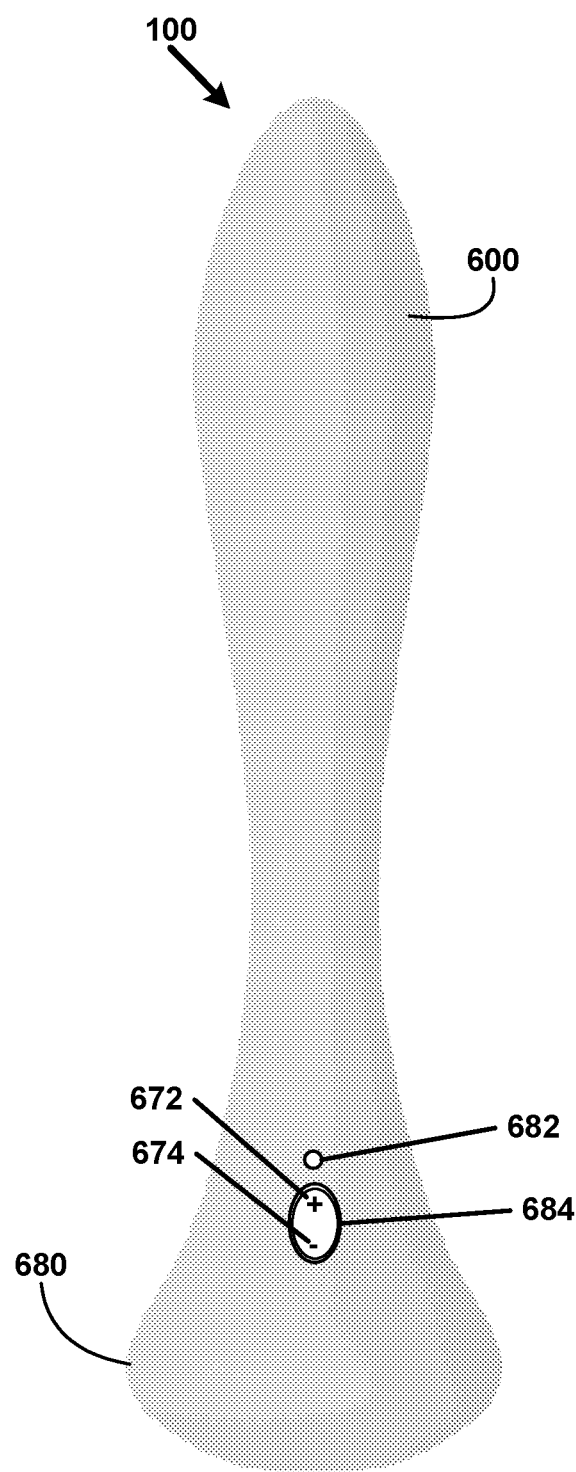
FIG. 6 shows for illustrative purposes only an example of a digitally enabled pelvic self-examination device of one embodiment.

A Digitally Enabled Pelvic Self-Examination Device:

FIG. 6 shows for illustrative purposes only an example of a digitally enabled pelvic self-examination device of one embodiment. FIG. 6 shows the digitally enabled pelvic self-examination device 100. The digitally enabled pelvic self-examination device 100 includes a proximal end with a camera 600. The device includes a zoom in +672 and zoom out −674 on a toggle switch to close in or back on a tissue. An external light diode indicating successful insertion and camera activation 682 can be included. A button for taking images and video through continuous hold with zoom in and out ability for better visualization 684 is included. The button includes a toggle switch to zoom in 672 and zoom out 674. The digitally enabled pelvic self-examination device 100 includes a distal end with a hand grip 680. The distal end with a hand grip 680 is grasped by the user for insertion. The proximal end has a camera 600 that preferably turns on when inserted in the vaginal area. The proximal end with a camera 600 turns off the camera with the digitally enabled pelvic self-examination device 100 is removed from the vaginal in one embodiment.

Figure 7A:
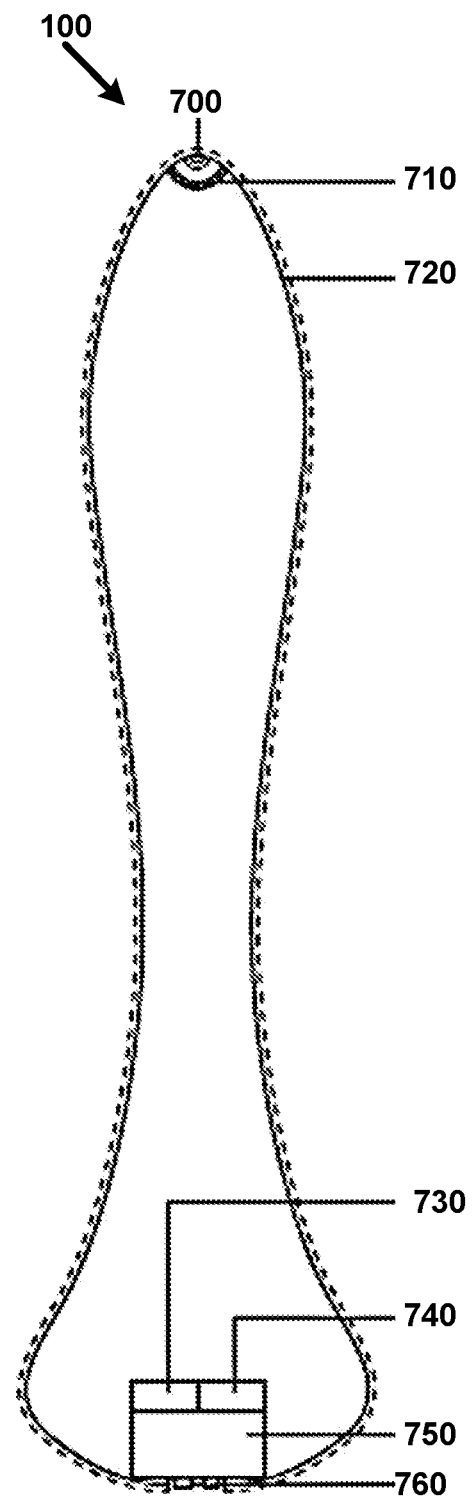
FIG. 7A shows for illustrative purposes only an example of an interior view of a digitally enabled pelvic self-examination device elements of one embodiment.

An Interior View of a Digitally Enabled Pelvic Self-Examination Device Elements:

FIG. 7A shows for illustrative purposes only an example of an interior view of a digitally enabled pelvic self-examination device elements of one embodiment. FIG. 7A shows the digitally enabled pelvic self-examination device 100 includes an endoscope camera with HD resolution and autofocus, resistant to moisture with 3D scanning ability and a light source/LED light 700. The digitally enabled pelvic self-examination device included a measurement detection for measuring distances and pressures to diagnose or treat pelvic prolapsis or dilation during childbirth 710.

A frame of the device, which could be 3D printed or be a lightweight metal material (aluminum) 720 can be included. Data collection and storage devices can be connected to a cloud with instant Wi-Fi/Bluetooth transfer for assessment, diagnosis and treatment pathways 730. Also, electronics can be included to support camera, lighting, wireless data transfer, heat and pressure detection 740. At least one rechargeable battery 750 is shown. A magnetic USB charging point 760 allows recharging of at least one rechargeable battery 750 of one embodiment.

Figure 7B:
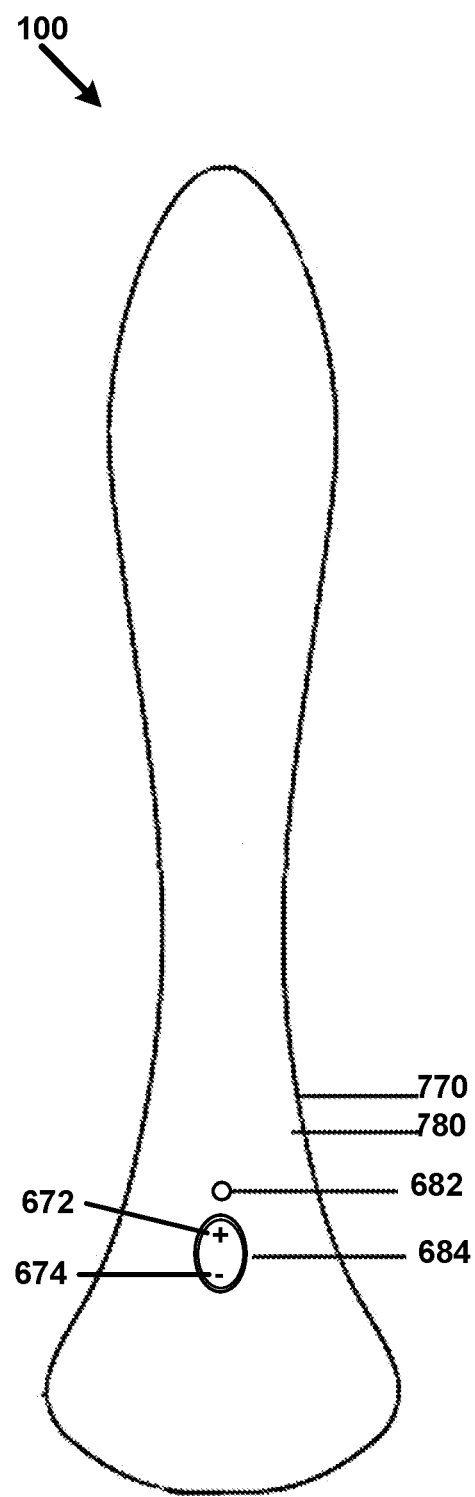
FIG. 7B shows for illustrative purposes only an example of an exterior view of a digitally enabled pelvic self-examination device elements of one embodiment.

Digitally Enabled Pelvic Self-Examination Device Elements:

FIG. 7B shows for illustrative purposes only an example of an exterior view of a digitally enabled pelvic self-examination device elements of one embodiment. FIG. 7B shows a condom to be applied before use 770 of the digitally enabled pelvic self-examination device 100 to prevent cross contamination of infectious diseases. Medically graded silicon, waterproof and wipe cleanable 780 outer cover can be used. An external light diode can be included indicating successful insertion and camera activation 682. A button for taking images and video through continuous hold with zoom in and out ability for better visualization 684 can be included. The button includes a toggle switch to zoom in 672 and zoom out 674 of one embodiment.

Figure 8A:
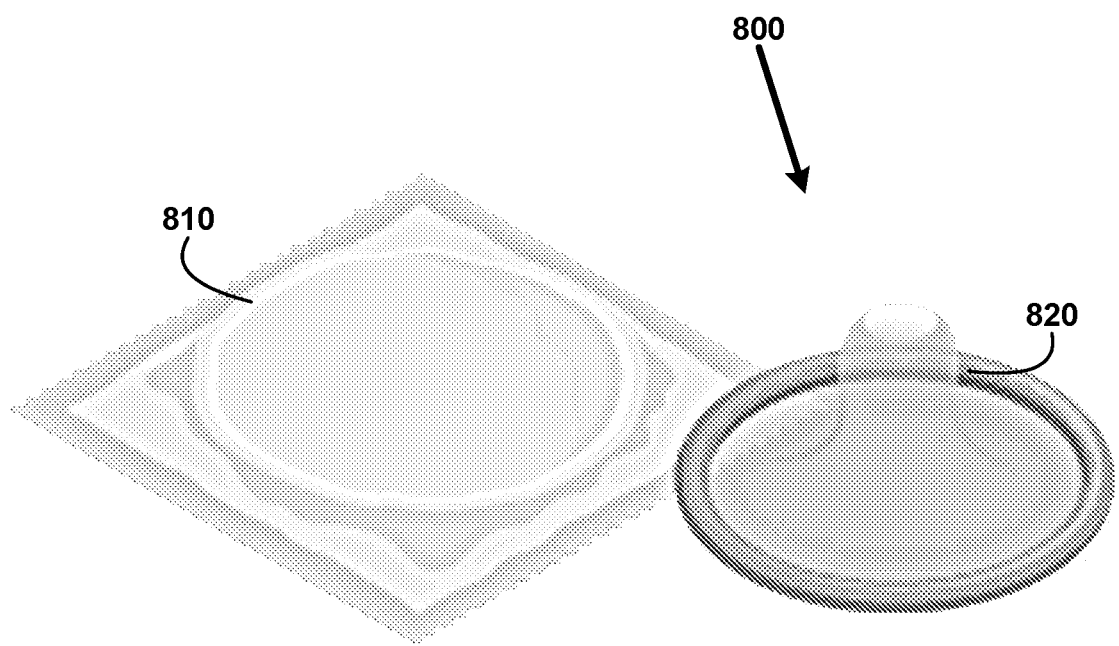
FIG. 8A shows for illustrative purposes only an example of a biodegradable cover over the digitally enabled pelvic self-examination device of one embodiment.

A Biodegradable Cover:

FIG. 8A shows for illustrative purposes only an example of a biodegradable cover over the digitally enabled pelvic self-examination device of one embodiment. FIG. 8A shows a biodegradable cover over the digitally enabled pelvic self-examination device 800. The biodegradable cover is also referred to as a condom without any change in meaning. The condom package 810 is a part of the kit the user receives from a clinician. The condom 820 is a one-time use element for pre-insertion application and post-insertion disposal. The condom 820 is placed over the digitally enabled pelvic self-examination device 100 of FIG. 1 from the proximal end to the distal end. The condom prevents germs and bacteria being transferred to other users. After use, the user can dispose of the condom and the condom will degrade in a land fill because it is made of a biodegradable material of one embodiment.

Figure 8B:
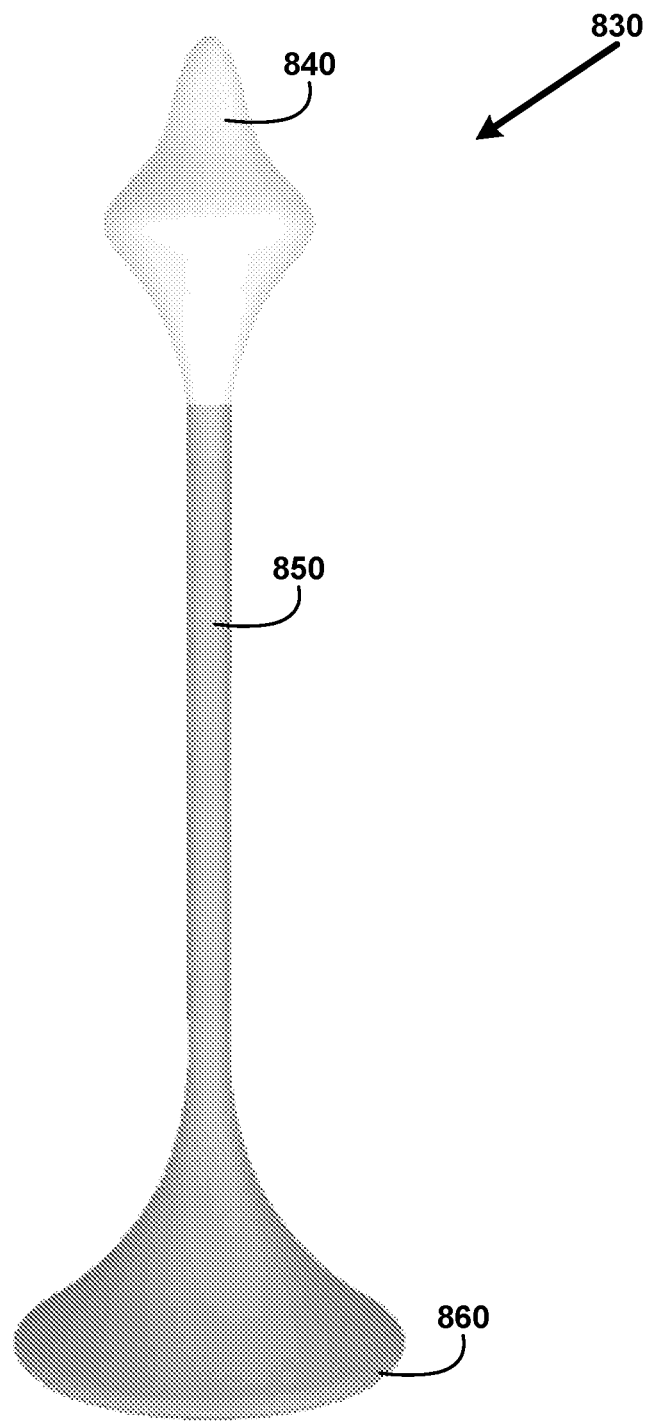
FIG. 8B shows for illustrative purposes only an example of a digitally enabled pelvic self-examination device swab of one embodiment.

Digitally Enabled Pelvic Self-Examination Device Swab:

FIG. 8B shows for illustrative purposes only an example of a digitally enabled pelvic self-examination device swab of one embodiment. FIG. 8B shows a digitally enabled pelvic self-examination device swab 830. The swab 840 is sampling device that couples to the attachment component that attaches to the digitally enabled pelvic self-examination device 100 of FIG. 1. The user can maneuver the swab 840 at a proximal end of the digitally enabled pelvic self-examination device swab 830 with an extension 850. The user grasps the distal end handle 860 to insert and maneuver the swab 840 to collect a cervical sample for clinical analysis.

The appearance of the cervix is affected by the user's menstrual cycle. The color, shape, texture, etc. of the cervix and other organs change during the monthly cycle. Early pregnancy, infections and disease also affect the appearance of the cervix. The user would know when their menstrual cycle is beginning and ending. They may become aware if they are pregnant, have an infection or are subject to a disease. The use of the digitally enabled pelvic self-examination device 100 of FIG. 1 for self-examination and particularly collecting a swab sample should be scheduled after the end of the menstrual cycle or well before the onset of the cycle.

The user should consult with their physician if pregnant; has an infection or disease as to the most appropriate time to perform the self-examination. The user should be aware of these conditions otherwise they may see unexpected changes in the images of their cervix that could be misinterpreted as something to be concerned about where in fact it is normal fluctuations caused by the temporary circumstances of one embodiment.

Figure 9A:
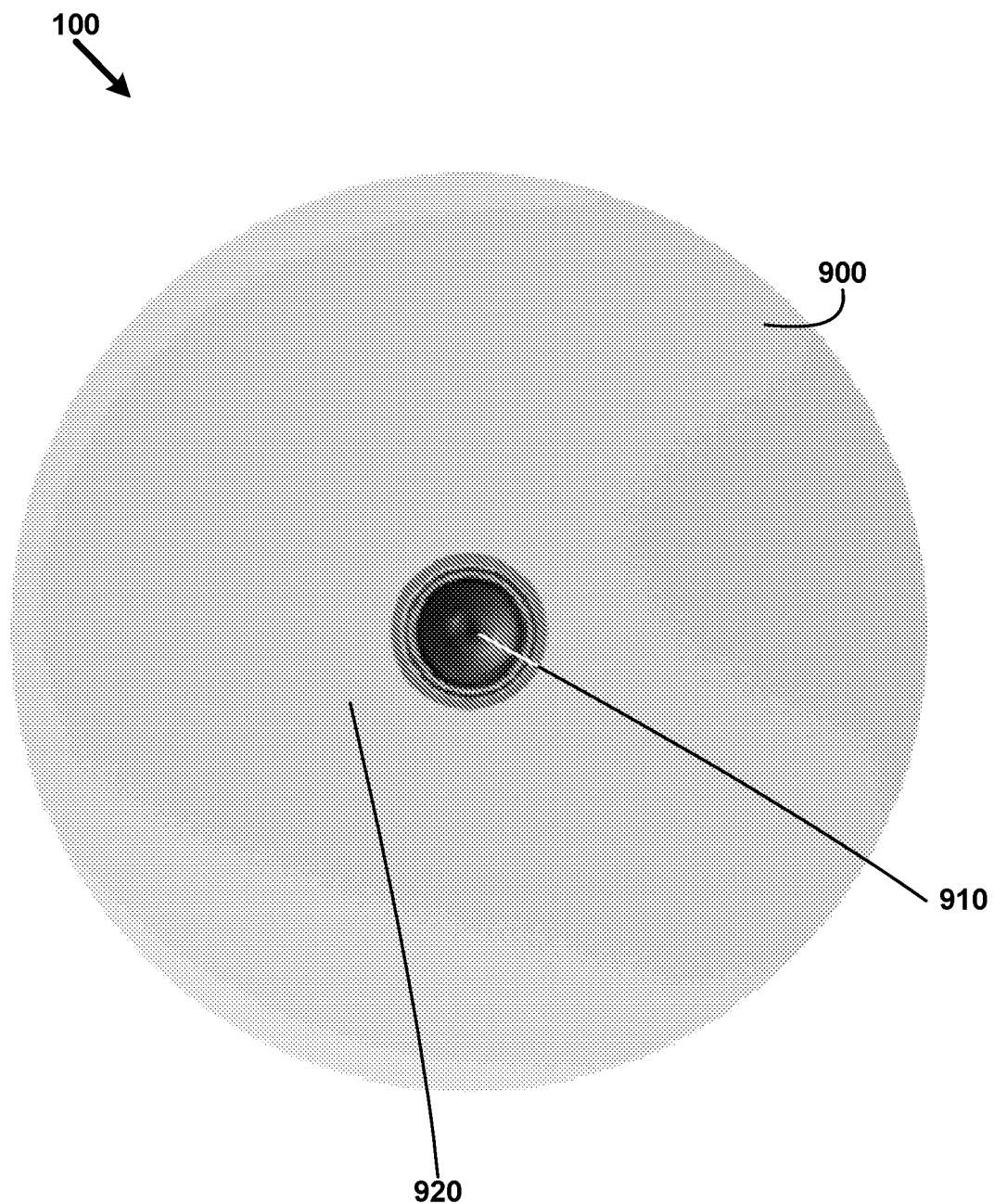
FIG. 9A shows for illustrative purposes only an example of a digitally enabled pelvic self-examination device camera with lights of one embodiment.

Digitally Enabled Pelvic Self-Examination Device Camera:

FIG. 9A shows for illustrative purposes only an example of a digitally enabled pelvic self-examination device camera with lights of one embodiment. FIG. 9A shows the proximal end of the device with LED light source 900. The LED light source is powered with the at least one rechargeable battery 750 of FIG. 7A. Also shown is a camera aperture 910 that opens to capture cervical images after the digitally enabled pelvic self-examination device 100 of FIG. 1 is inserted. The LED lights illumination 920 is shown that illuminate pelvic areas for capturing photographs and videos. The camera acquired images are used for diagnostic analysis of the medical status of a user's cervix of one embodiment. In another embodiment, suitable illumination devices can be used, such as an infrared camera lens arrangement to aid in viewing internal areas. These digital visual examinations include examinations of the colon and the anus for anal fissures, polyps, hemorrhoids and other abnormalities of the anus and lower colon.

Figure 9B:
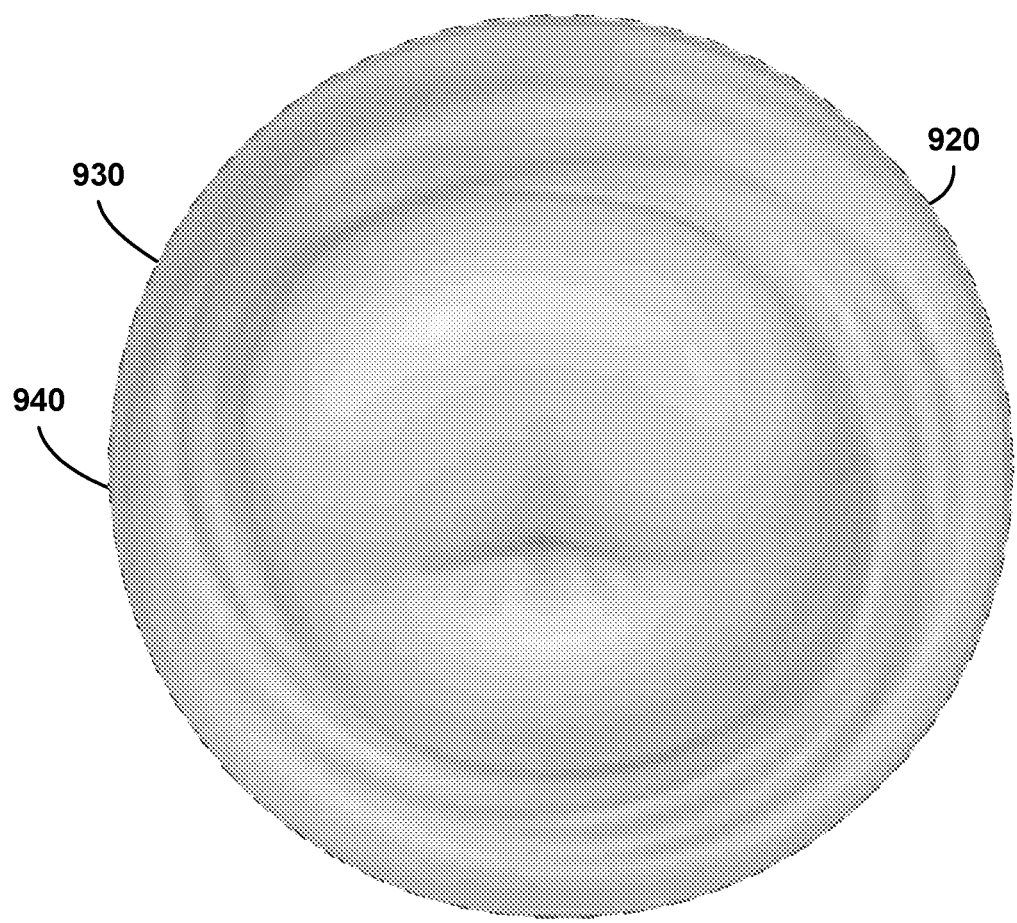
FIG. 9B shows for illustrative purposes only an example of a digitally enabled pelvic self-examination device camera cervical image of one embodiment.

Digitally Enabled Pelvic Self-Examination Device Camera Cervical Image:

FIG. 9B shows for illustrative purposes only an example of a digitally enabled pelvic self-examination device camera cervical image of one embodiment. FIG. 9B shows a uterine cervix image 920 captured with the endoscope multispectral camera (with microscopic function and HD resolution with autofocus), resistant to moisture 312 of FIG. 3. The uterine cervix image 920 can be a single, or multiple, photographs of the cervix. The uterine cervix image 920 can be a video including a 3D scanning video. The images including single, or multiple, photographs and videos including 3D scanning videos can be recorded.

In addition, the images can include superimposed heat detection temperature readings using the mobile application. The recorded images allow the user to share the images and data with their physician and clinician remotely. In some instances, the user may be bed ridden, lack transportation to a medical office, clinic or hospital, or have mobility difficulties. The self-examination ability of the digitally enabled pelvic self-examination device 100 of FIG. 1 user solves these obstacles.

It further makes available cervical cancer and other vaginal conditions screenings to take place conveniently and with less pain and apprehension for the user. The remote physician or clinician can discuss the images and data with the user to advise them of possible future actions based on the initial findings, suggest and order prescriptions for treatment of any discomfort felt by the user. The remote physician or clinician can arrange for pickup of a swab sample taken by the user and confirmed by images of that sampling taking place by the user.

A benefit to the user is that a physician, generally a gynecologist, performs a great deal of vaginal examinations during a year. Most women have one pelvic exam per year. It is extremely unlikely that the physician would remember what the user's cervix looked like a year earlier after examining what could be hundreds if not a thousand other women's cervixes during the preceding year.

The digitally enabled pelvic self-examination device 100 of FIG. 1 provides the user with the means to more frequent self-examinations during the year. Additionally, recording the camera images provides the user with comparative images to determine any changes. Those same recorded comparative images can be shared with the physician to prevent any misdiagnosis due to a physician's unclear recollection of the user's previous examination results. The user is better able to become closely familiar with their internal vaginal interior landscape than the user herself.

The user has more time available than a short doctor visit be closely view the images and data collected to determine any changes that may be of concern. The user has the opportunity for more frequent self-examinations than could be practical or financially feasible with doctor visits. The accumulation of recorded images and data along a timeline that would show a progression of the changes taking place which may be a further clue as to the nature and stage of any changes. The user now becomes the sentinel of their own health which may in fact save their life.

The uterine cervical bulge 930 is seen in the uterine cervix image 920. A uterine cervical bulge 930 may be an indication of uterine prolapse that occurs when pelvic floor muscles and ligaments stretch and weaken until they no longer provide enough support for the uterus. As a result, the uterus slips down into or protrudes out of the vagina. Uterine prolapse most often affects people after menopause that has had one or more vaginal deliveries. This camera images, swabbed samples and measurement functions will be used for a diagnostic analysis to assess conditions including uterine prolapse, cervical cancer, colposcopy and other conditions. A cervical depression 940 is another condition that will be analyzed with the camera images, swabbed samples and measurement functions.

The digitally enabled pelvic self-examination device 100 of FIG. 1 is an alternative to physician vaginal speculum examinations commonly used during pelvic exams and Pap smears. A large number of women find vaginal speculum examinations intrusive, painful, something to fear, and a violation of their privacy. The evidence of this is the missed appointments of vaginal speculum examinations despite the importance of vaginal and cervix examinations that may prevent death, preventable with early detection of conditions including cancer. The user self-examinations provide the information including camera images, measurements and user collected vaginal and cervical samples used for accurate diagnostic analyses benefitting the users.

The benefits extend to the healthcare professionals. For example, a physician may have multiple women performing self-examinations while sitting at their desk reviewing diagnostic results. In current typical pelvic exams and Pap smears the physician must perform the examination personally thereby reducing the number of women that may be able to complete cervical cancer screenings appointments. More frequent cervical cancer screenings can significantly reduce cervical cancer if women can achieve more frequent screenings. Reducing and eliminating the fear, pain and intrusive concerns of women currently leading to missed appointments will accommodate the concerns of women and provide a positive response to keeping the screening appointments and even increase screening to lead to early detection.

User surveys show the depth of concerns. For example, women use the following terms to describe the feeling toward vaginal speculum examinations. A few of the large number of expressions are intrusive, dread, cervix, painful, hurt, instrument out dated, ugh, weird, yuck, harm device, inspection, invasion, large, expansion, old fashioned, nervous, scratching, and torture-like. Clinicians refer to the speculum as pain, challenging, discomfort, plastic, metal, daunting, invasive, intrusive, harm, hurt, fear, and otherworldly of one embodiment.

A user performing self-examinations, for example, at home may see in the images something that appears different than the surrounding tissues. Rather than become overwhelmed with worry the user can contact a physician or clinician to express the users concerns. The recorded images and data taken by the user can be transmitted to the physician or clinician via WIFI. The physician or clinician upon viewing the images and data in their remote discussion with the user may be able to allay the users concerns or recommend making a swab to send in for further laboratory analysis.

Figure 10:
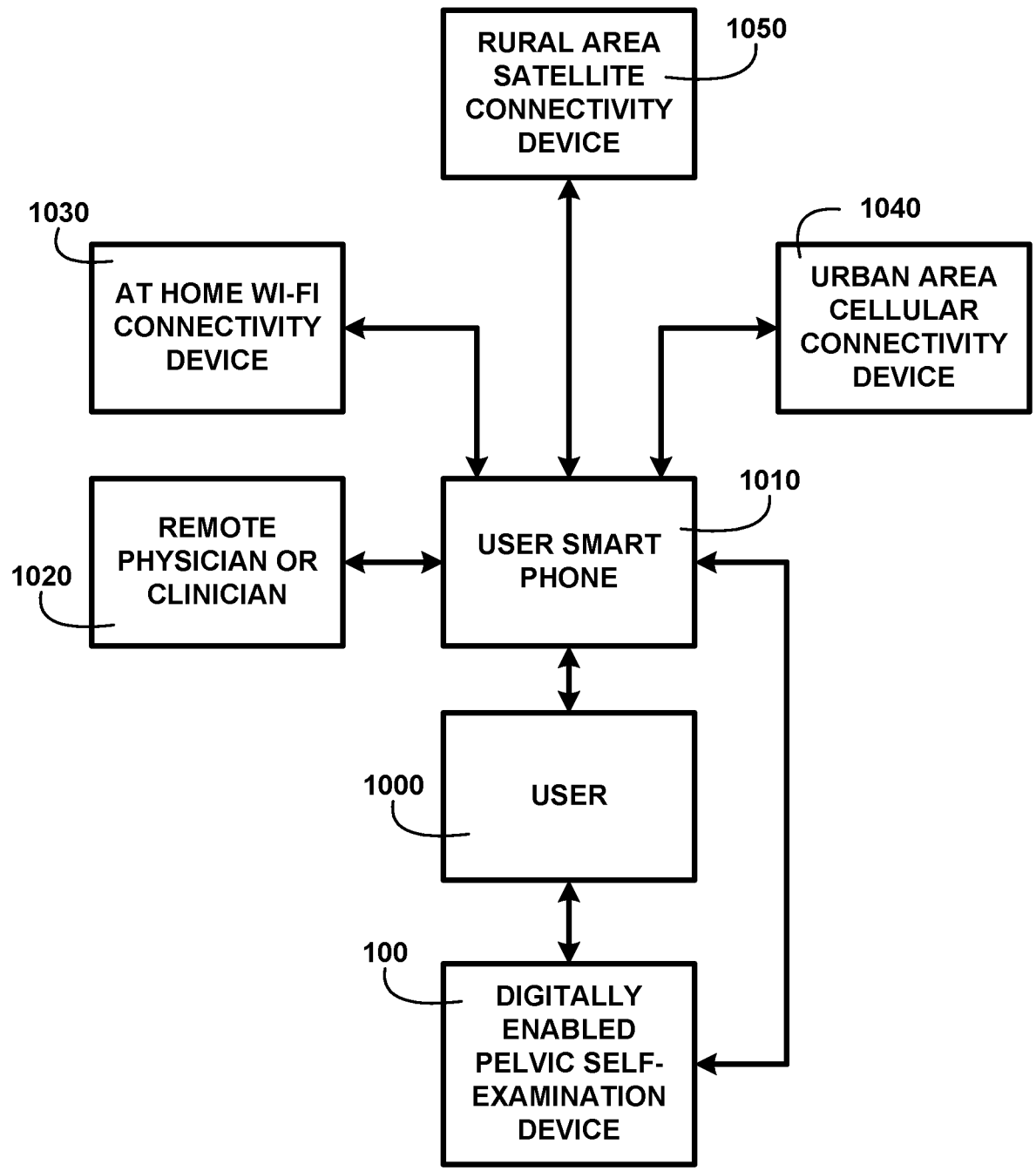
FIG. 10 shows a block diagram of an overview of digitally enabled pelvic assessment and diagnosis device communication connectivity of one embodiment.

Digitally Enabled Pelvic Assessment and Diagnosis Device Communication Connectivity:

FIG. 10 shows a block diagram of an overview of digitally enabled pelvic assessment and diagnosis device communication connectivity of one embodiment. FIG. 10 shows the digitally enabled pelvic self-examination device 100 being used by a user 1000. The digitally enabled pelvic self-examination device 100, when inserted into the user 1000 vagina, can capture, record and transmit photographic and video images to the user smart phone 1010. Also transmitted are heat detection temperatures of the cervix. The heat detection temperatures are superimposed on the photographic and video images. The mobile application operating on a user's smart phone 1010 can transmit the photographic and video images with superimposed heat detection temperatures to a remote physician or clinician 1020. The mobile application operating on the user's smart phone 1010 can establish through the application communication to the remote physician or clinician 1020. The user 1000 may be located at home performing the self-examination. The user 1000 may connected to an at home WIFI connectivity device 1030. The user 1000 may be located in a town or city that provides service to the user 1000 with an urban area cellular connectivity device 1040.

In some instances, the user 1000 may be located in a remote area without WIFI or cellular service. In remote areas the user 1000 communication may be established a rural area satellite connectivity device 1050. Regardless of the type of communication service available, the user 1000 and the remote physician or clinician 1020 can simultaneously view the images and data of the user 1000 self-examination. They can discuss the condition of the user 1000 cervix and determine any next steps in treatment and arrange for the transport of any swabbed sample for laboratory analysis of one embodiment.

Figure 11:
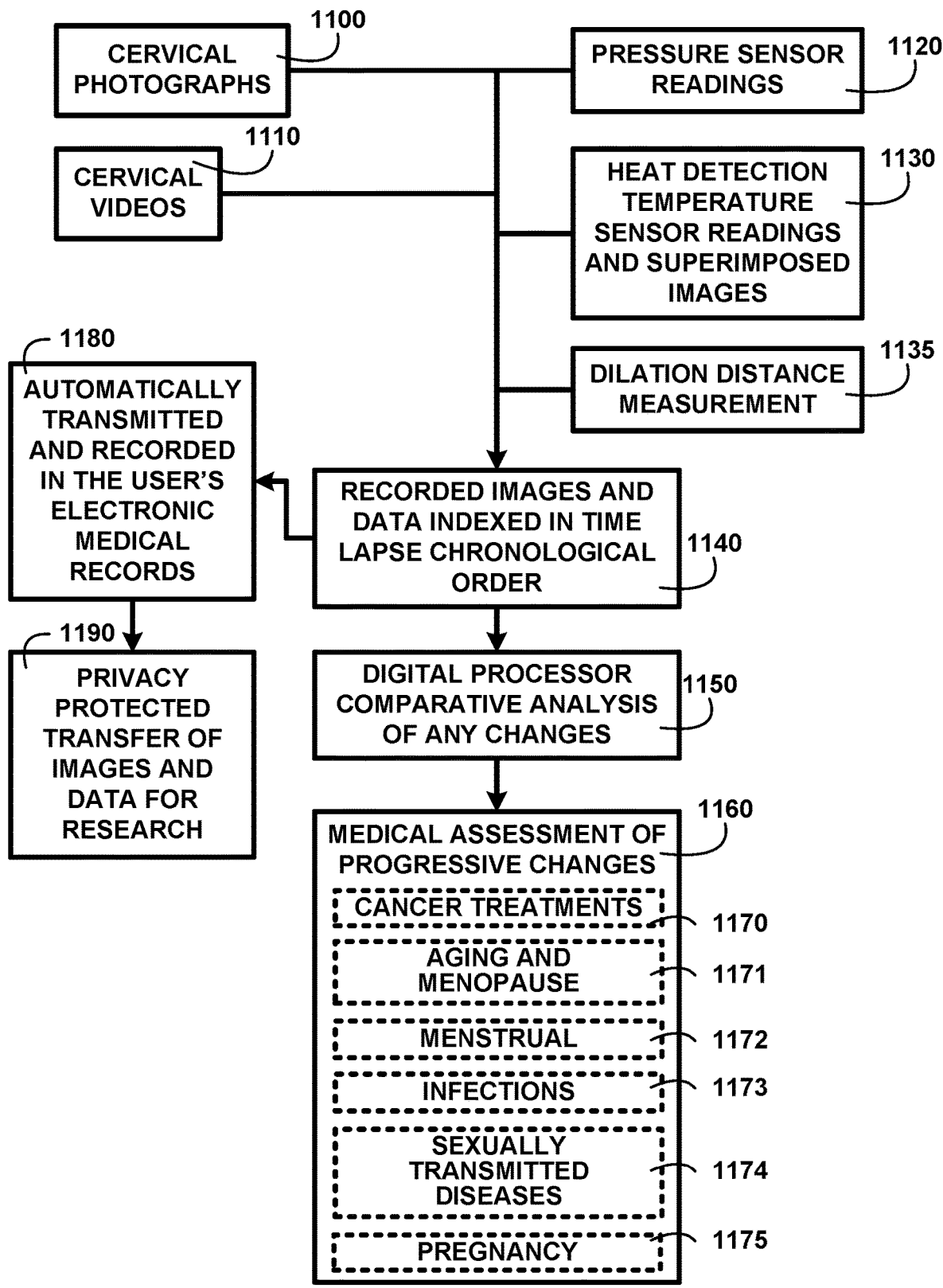
FIG. 11 shows a block diagram of an overview of user's electronic medical records of one embodiment.

User's Electronic Medical Records:

FIG. 11 shows a block diagram of an overview of user's electronic medical records of one embodiment. FIG. 11 shows automatic transfer of the information to digital medical records when a user takes cervical photographs 1100, cervical videos 1110. After the digitally enabled pelvic assessment and diagnosis device 100 of FIG. 1 has performed the pressure sensor readings 1120, heat detection temperature sensor readings and superimposed images 1130, dilation distance measurement 1135, the images and data can be recorded in memory. The memory includes recorded images and data indexed in time lapse chronological order 1140.

A digital processor comparative analysis of any changes 1150 is perform in a computer to determine any changes detected in the images and sensor data. A medical assessment of progressive changes 1160 in for example cancer treatments 1170, aging and menopause 1171, menstrual 1172, infections 1173, sexually transmitted diseases 1174, and pregnancy 1175 are reported to the user and their physician. The captured images, data collected and comparative analysis is automatically transmitted and recorded in the user's electronic medical records 1180. Privacy protected transfer of images and data for research 1190 is made to advance the knowledge base for advances in these areas of research of one embodiment.

Figure 12:
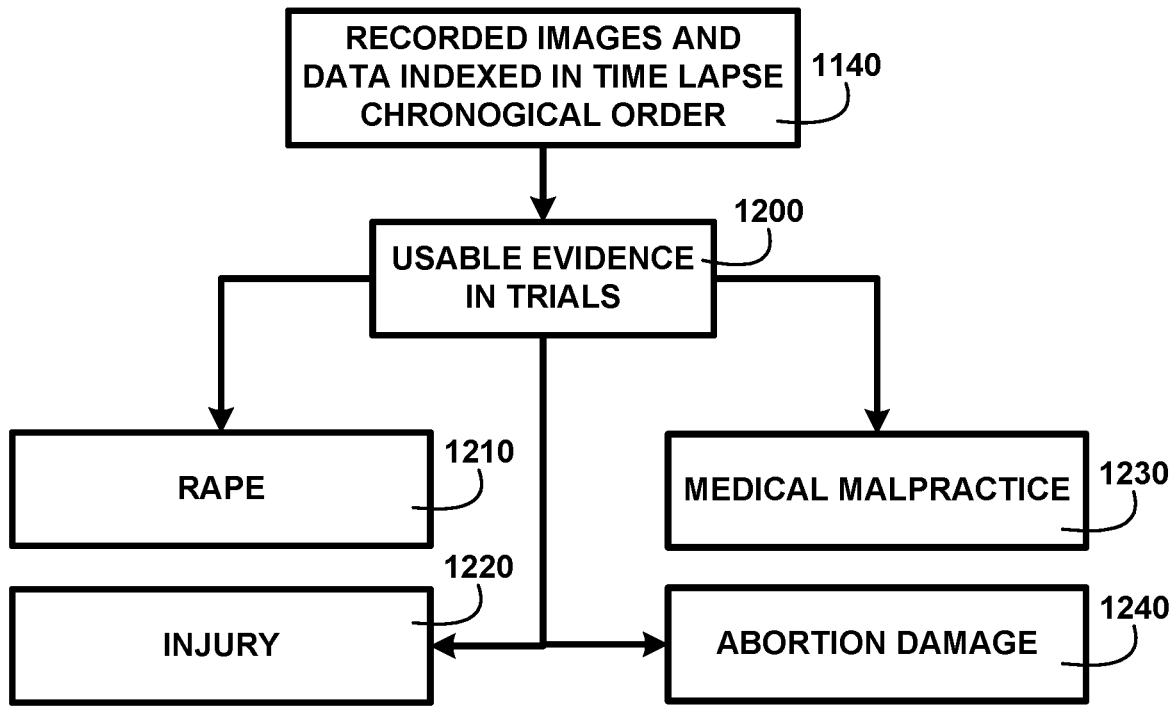
FIG. 12 shows a block diagram of an overview of time lapse chorological order data of one embodiment.

Time Lapse Chronological Order Data:

FIG. 12 shows a block diagram of an overview of time lapse chronological order data of one embodiment. FIG. 12 shows recorded images and data indexed in time lapse chronological order data 1140. This can be used in legal cases as evidence. The images and time lapse differences of vaginal conditions before and after an incident will show the damage and extent of the damage and may be admissible and usable evidence in trials 1200. For example, along with a rape kit and DNA evidence in a rape 1210, injury 1220 case, medical malpractice 1230 and surgical abortion damage 1240 this may be documented evidence of a before and after condition of the user of one embodiment.

Figure 13:
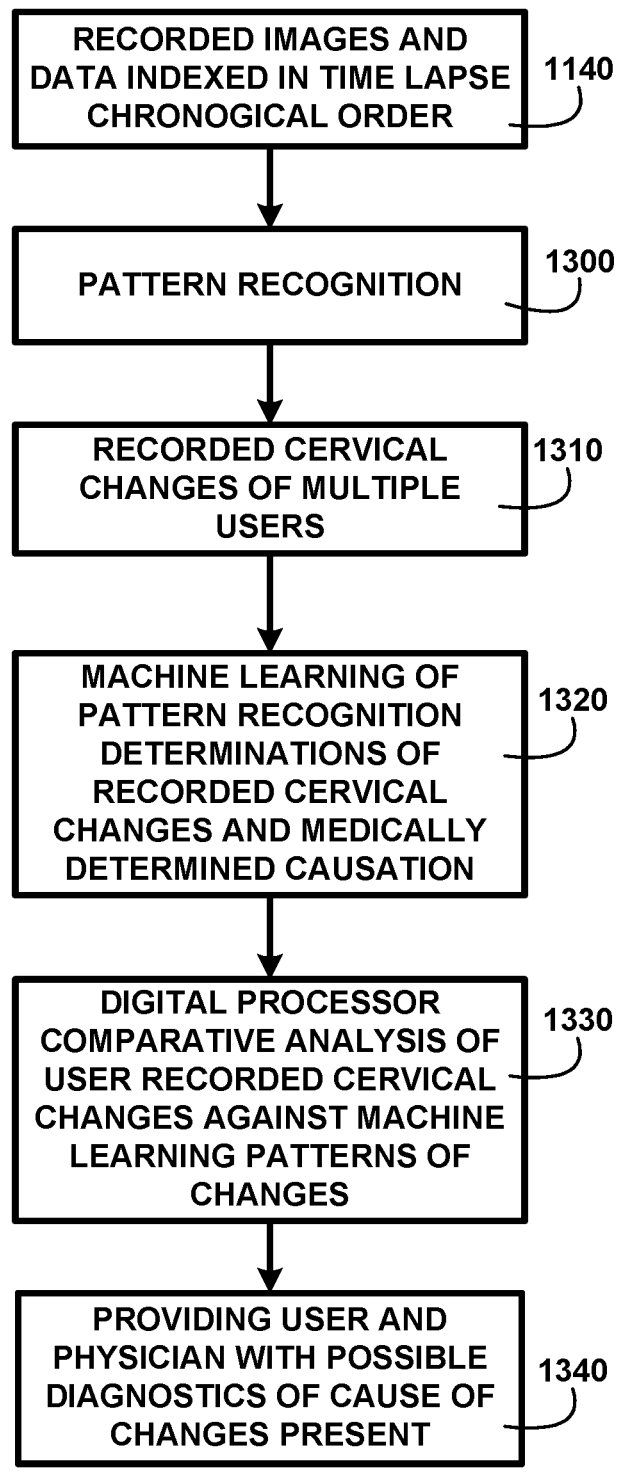
FIG. 13 shows a block diagram of an overview of pattern recognition of one embodiment.

Pattern Recognition:

FIG. 13 shows a block diagram of an overview of pattern recognition of one embodiment. FIG. 13 shows recorded images and data indexed in time lapse chronological order 1140. Pattern recognition 1300 is a data analysis method that uses machine learning algorithms to automatically recognize patterns and regularities in data. The recorded cervical changes of multiple users 1310 can be processed with machine learning of pattern recognition determinations of recorded cervical changes and medically determined causation 1320. Digital processor comparative analysis of user recorded cervical changes against machine learning patterns of changes 1330 can use pattern recognition to identify possible causes of the user condition. The results will be providing user and physician with possible diagnostics of cause of changes present 1340 of one embodiment.

Figure 14:
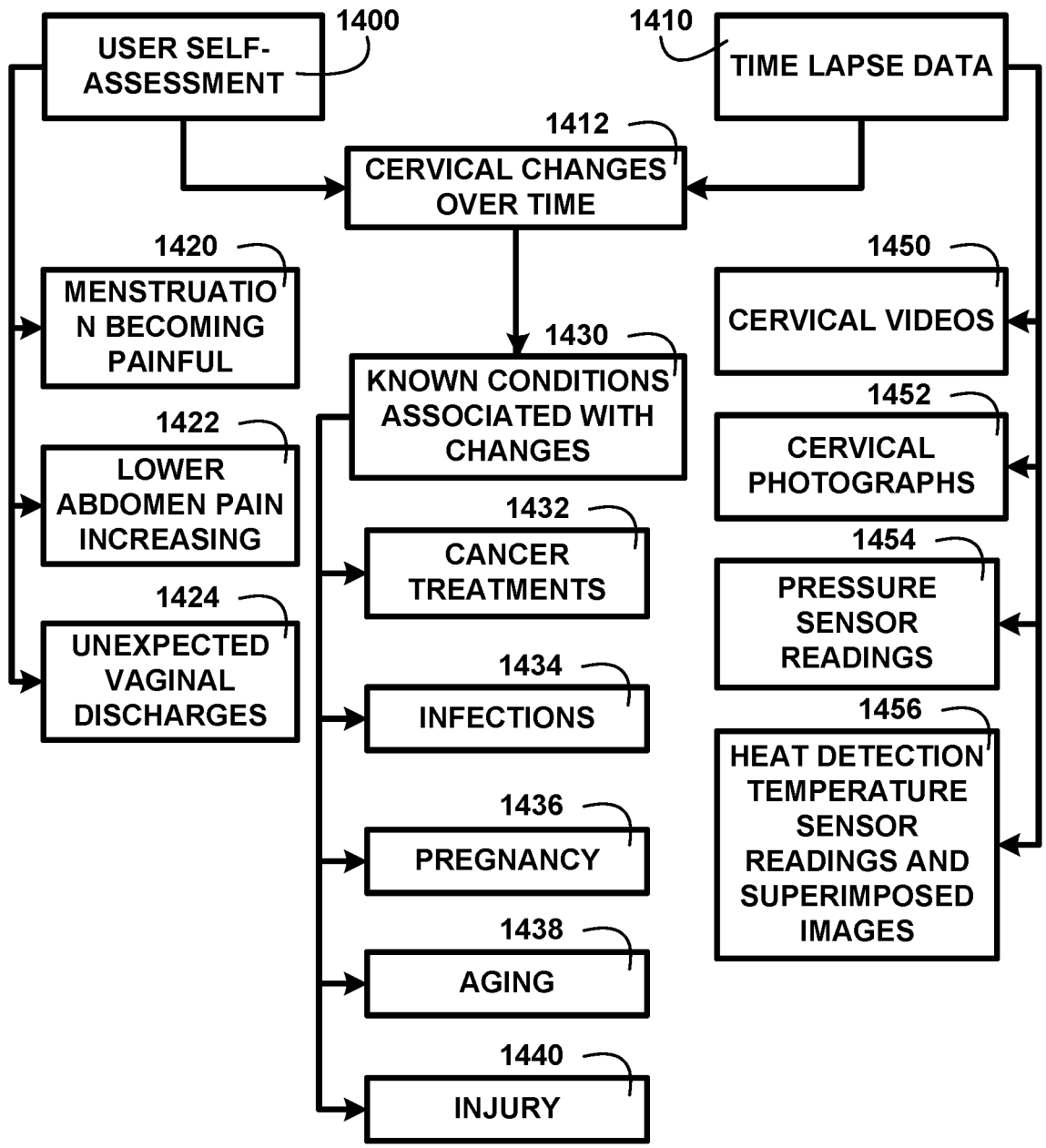
FIG. 14 shows a block diagram of an overview of user self-assessment of one embodiment.

User Self-Assessment:

FIG. 14 shows a block diagram of an overview of user self-assessment of one embodiment. FIG. 14 shows a user self-assessment 1400 being combined with time lapse data 1410 showing cervical changes over time 1412. The user self-assessment 1400 may include menstruation becoming painful 1420, lower abdomen pain increasing 1422 or unexpected vaginal discharges 1424. Known conditions associated with changes 1430 may include cancer treatments 1432, infections 1434, pregnancy 1436, aging 1438, or injury 1440.

The recorded images and data form a time lapse of any changes with the cervical videos 1450, cervical photographs 1452, pressure sensor readings 1454 and heat detection temperature sensor readings and superimposed images 1456. These changes over time will provide a progression of any condition the clinician can review to account of the cause of the self-assessed condition of the user. The time lapse progression may also reflect an unknown condition that necessitates addition examination to detect the cause of one embodiment.

Figure 15:
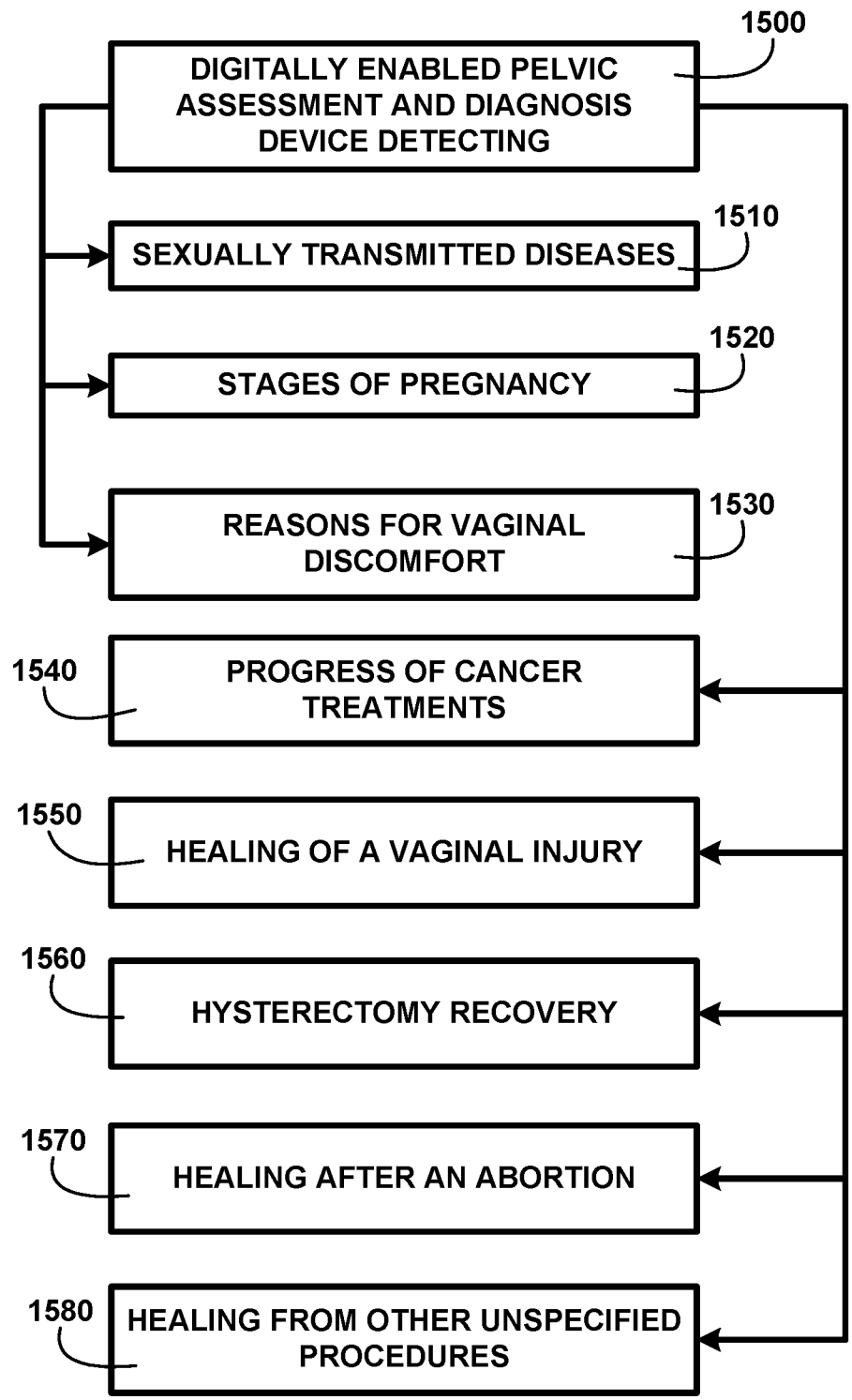
FIG. 15 shows a block diagram of an overview of healing and treatment follow-up of one embodiment.

Healing and Treatment Follow-Up:

FIG. 15 shows a block diagram of an overview of healing and treatment follow-up of one embodiment. FIG. 15 shows digitally enabled pelvic assessment and diagnosis device detecting 1500 sexually transmitted diseases 1510, stages of pregnancy 1520, reasons for vaginal discomfort 1530, progress of cancer treatments 1540, healing of a vaginal injury 1550, and hysterectomy recovery 1560, healing after an abortion 1570, and healing from other unspecified procedures 1580. The images and data can reveal improvements after treatment of a condition and may detect slow progress of recovery that may require change in medication or other means to progress the healing process of one embodiment.

Figure 16:
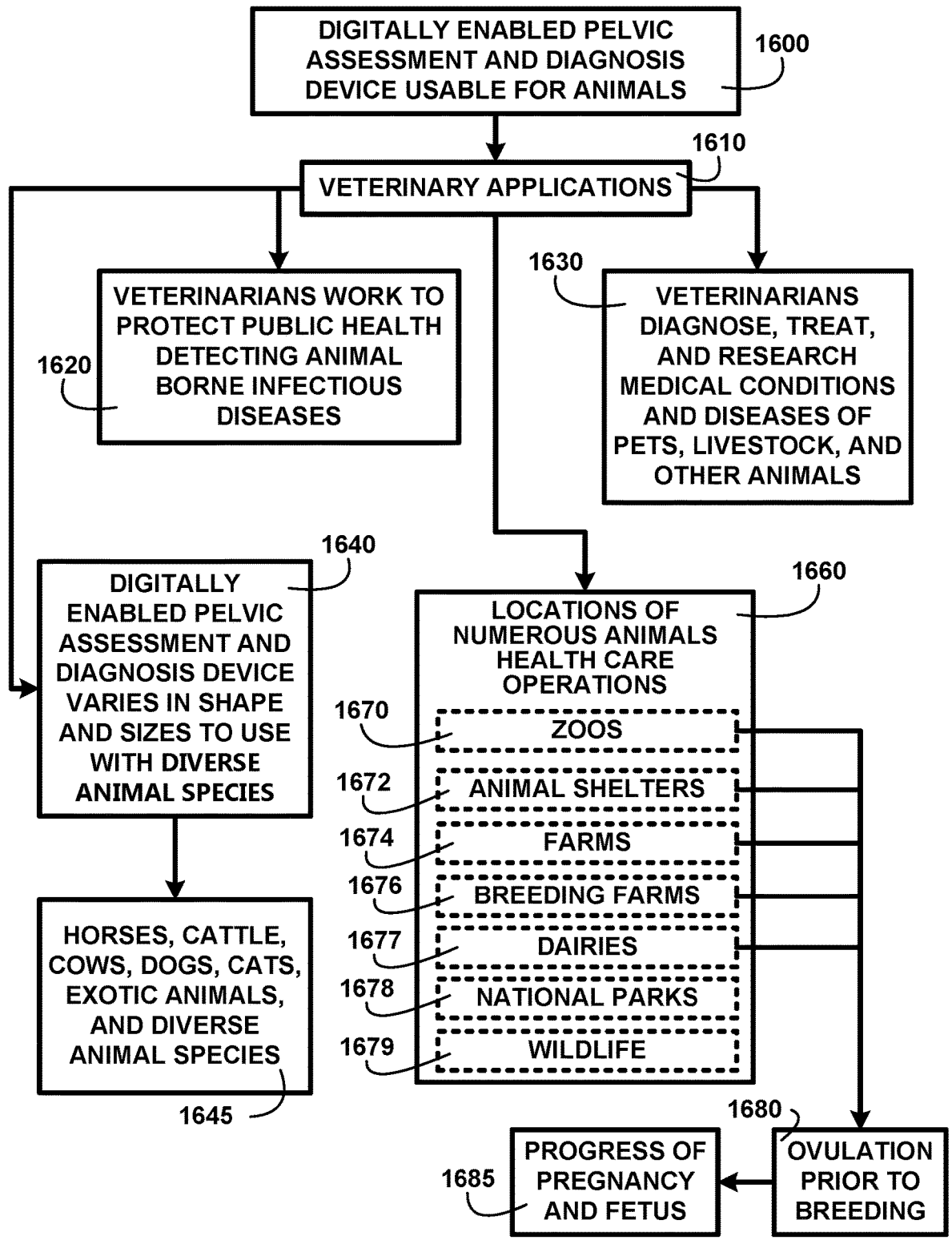
FIG. 16 shows a block diagram of an overview of veterinary applications of one embodiment.

Veterinary Applications:

FIG. 16 shows a block diagram of an overview of veterinary applications of one embodiment. FIG. 16 shows digitally enabled pelvic assessment and diagnosis device usable for animals 1600. Veterinary applications 1610 include veterinarians work to protect public health detecting animal borne infectious diseases 1620. Veterinarians diagnose, treat, and research medical conditions and diseases of pets, livestock, and other animals 1630. The digitally enabled pelvic assessment and diagnosis device varies in shape and sizes to use with numerous animals 1640 for example horses, cattle, cows, dogs, cats, exotic animals, and diverse animal species 1645. Locations of numerous animals' health care operations 1660 include zoos 1670, animal shelters 1672, farms 1674, breeding farms 1676, dairies 1677, national parks 1678, and wildlife 1679. Most of these locations involve animal care for breeding of endangered species and various livestock. The breeding can be enhance with vaginal examination with the digitally enabled pelvic assessment and diagnosis device 100 of FIG. 1 to check ovulation prior to breeding 1680 and progress of pregnancy and fetus 1685 of one embodiment.

Figure 17:
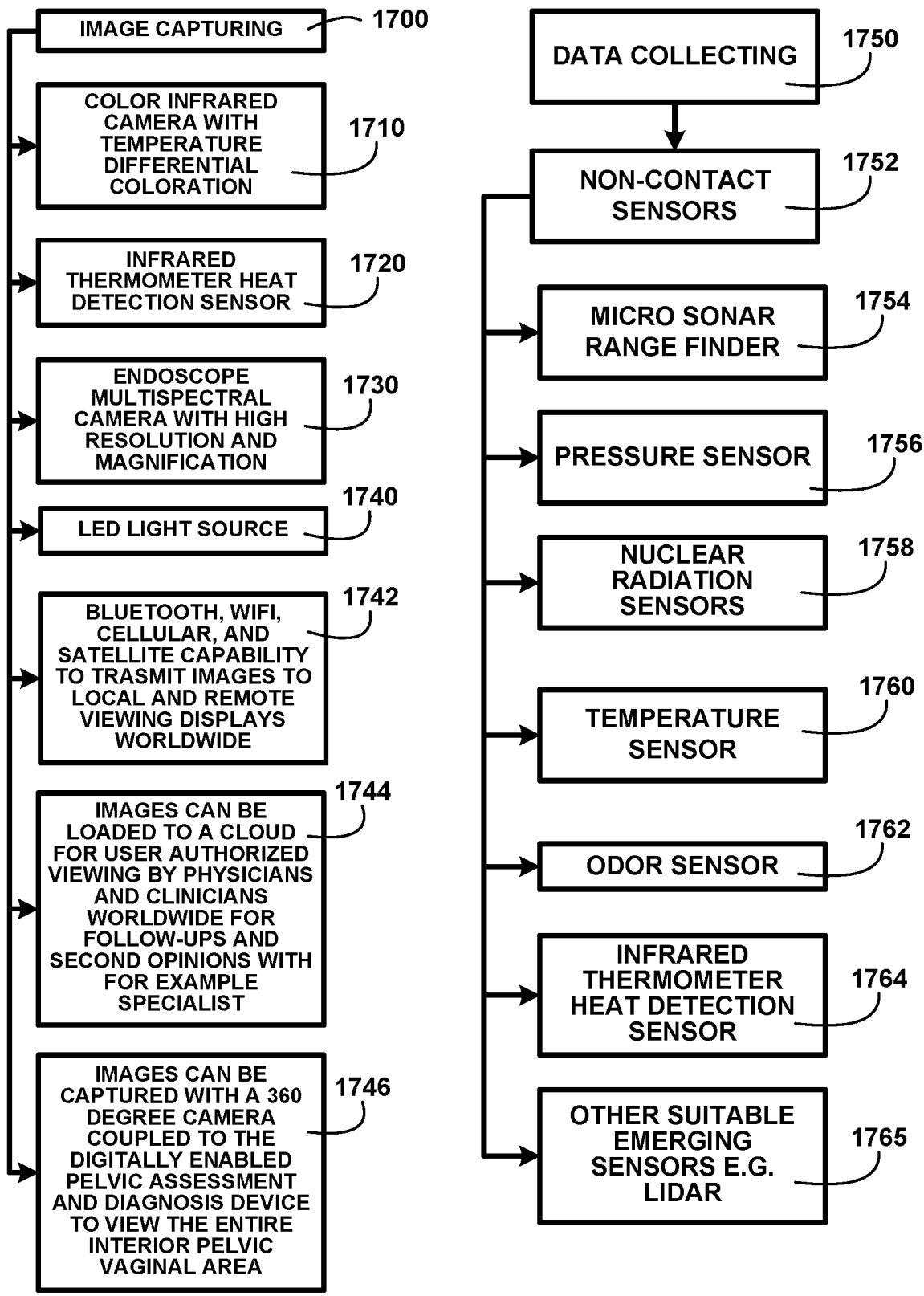
FIG. 17 shows a block diagram of an overview of image capturing and data collecting of one embodiment.

Image Capturing and Data Collecting:

FIG. 17 shows a block diagram of an overview of image capturing and data collecting of one embodiment. FIG. 17 shows examples of devices used for image capturing 1700. Image capturing 1700 can include the use of color infrared camera with temperature differential coloration 1710 and an infrared thermometer heat detection sensor 1720. These will provide colorized images showing temperature variation. An endoscope multispectral camera 1730 with an LED light source 1740 will capture visible light images and videos for review. Bluetooth, WI-FI, cellular, and satellite capability to transmit images to local and remote viewing displays worldwide 1742. Images can be loaded to a cloud for user authorized viewing by physicians and clinicians worldwide for follow-ups and second opinions with for example specialist 1744. In one embodiment, photographic and video images can be captured with a 360 degree camera coupled to the digitally enabled pelvic assessment and diagnosis device to view the entire interior pelvic vaginal area 1746.

Data collecting 1750 includes non-contact sensors 1752 including micro sonar range finder 1754 to measure distances. A digital pressure sensor 1756 can be used to measure pressures that may indicate pelvic organ prolapse. Nuclear radiation sensors 1758 can measure radiation level during cancer treatments for cervical cancer. A temperature sensor 1760 can detect temperature that may indicate a change. An odor sensor 1762 may detect a condition that indicates infection. An infrared thermometer heat detection sensor 1764 and other suitable emerging sensors e.g. LiDAR may not only show temperature but the specific areas of elevated temperature with an infrared image of one embodiment.

Figure 18:
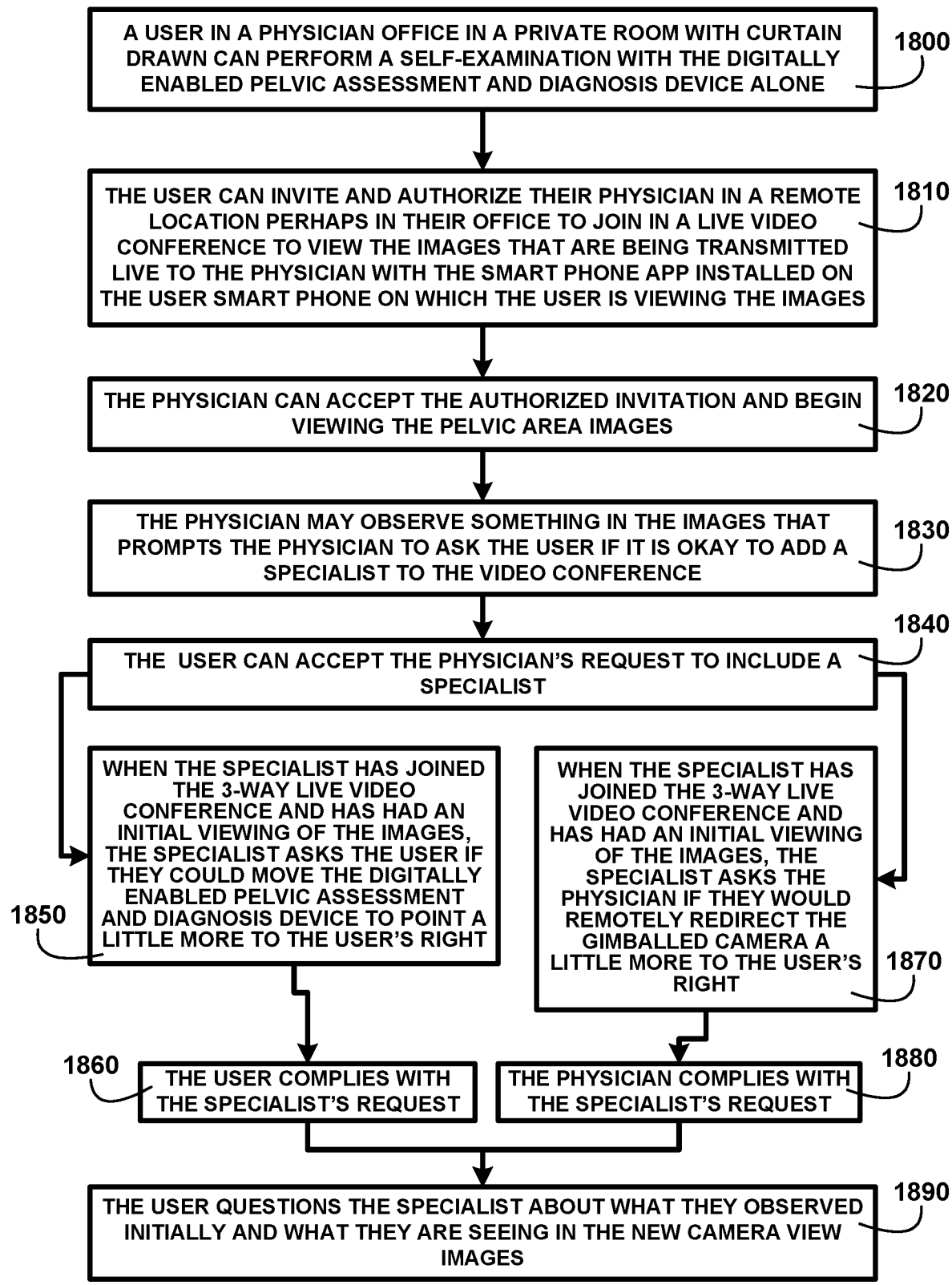
FIG. 18 shows a block diagram of an overview of live video conferencing of one embodiment.

Live Video Conferencing:

FIG. 18 shows a block diagram of an overview of live video conferencing of one embodiment. FIG. 18 shows a user in a physician office in a private room with curtain drawn can perform a self-examination with the digitally enabled pelvic assessment and diagnosis device alone 1800. The user can invite and authorize their physician in a remote location perhaps in their office to join in a live video conference to view the images that are being transmitted live to the physician with the smart phone app installed on the user smart phone on which the user is viewing the images 1810. A voice to text device and a language translation device are used for converting voice conversation to text and foreign language translations of the text during a video conference transmission of the pelvic images and videos and stored data. This allows for international video conferencing with a physician or specialist in another country to participant in the consultation with language becoming an obstacle. Secondly, this allows the user, physician and specialist to review the video conference discussions at a later date or time. The mobile application will also record the conversation as spoken to be recorded. This allows any discrepancy in the translations to be reviewed for proper idiomatic differences due to regional or dialectic language variations. The remote physician can use a remote mobile application on his/her mobile device to video conference with the user. The camera of the remote physician's mobile device can capture the remote physician's view and the camera of the user's mobile device can capture the face of the user while video conferencing. Both the user and the remote physician would be digitally and video connected via their respective connected mobile applications. The physician can accept the authorized invitation and begin viewing the pelvic area images 1820. The physician may observe something in the images that prompts the physician to ask the user if it is okay to add a specialist to the video conference 1830. The user can accept the physician's request to include a specialist 1840.

When the specialist has joined the 3-way live video conference and has had an initial viewing of the images, the specialist can ask the user if they could move the digitally enabled pelvic assessment and diagnosis device to point a little more to the user's right 1850. The user complies with the specialist request 1860. When the specialist has joined the 3-way live video conference and has had an initial viewing of the images, the specialist asks the physician if they would remotely redirect the gimbaled camera a little more to the user's right 1870. The physician complies with the specialist request 1880. The user questions the specialist about what they observed initially and what they are seeing in the new camera view images 1890. The user gets to share the images and data being collected right away with the physician while performing a private self-examination.

In another embodiment, the physician can save time by going to an exam room and view the images and data. When confronted with images that are unclear as to its indications, the physician can immediately seek a consultation with a specialist that may be some distance away and even in another country. The specialist can guide and confer and agree or disagree immediately with the physician remotely. All three of the live video conferencing aspects allows immediate access to the images and data.

In another embodiment, the digitally enabled pelvic assessment and diagnosis device includes an internal gimbal connected to the camera lens and an articulation motor. In this embodiment, both the end user and the remote physician and/or specialist are connected to the digitally enabled pelvic assessment and diagnosis device via their own respective mobile application. This allows the remote physician and/or a remote specialist to access the internal gimbal via remote software remote controls on their mobile application to remotely articulate and manipulate the camera lens as the user holds the device steady. The ability to remotely control the inserted digitally enabled pelvic assessment and diagnosis device allows the remote physician and/or remote specialist to access desired camera field of visions for a more thorough examination. As such, the digitally enabled pelvic assessment and diagnosis device allows the user to have a private diagnosis without a painful pelvic exam, as well as a consultation with a specialist that might otherwise take weeks or even months to occur.

The foregoing has described the principles, embodiments and modes of operation of the present invention should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. A device for self-examination of internal organs, comprising:
    an enclosed camera having an internal gimbal coupled to a light source and configured to capture views of the internal organs;
    a first remote application operating on a first remote mobile device of a first user and wirelessly coupled to the enclosed camera, the internal gimbal, and the light source and configured to allow the first user to display the captured views in real-time and remotely operate and control the enclosed camera and the light source and manipulate the internal gimbal to show a first set of views of the internal organs;
    a second remote application operating on a second remote mobile device of a second user and wirelessly coupled to the first remote application, wherein the second remote application is configured to allow the second remote user to remotely control the light sources and articulate and manipulate the internal gimbal independently from the first user to show a second set of views of the internal organs while the first user is communicating with the second user, wherein the second set of views are displayed to the first user via the first remote application and to the second user via the second remote application;
    a swabbing device removably coupled to the device and wirelessly coupled to the first and second remote applications and configured to allow the second user to remotely initiate collection of the internal pelvic cavity of pelvic cytology fluid and non-biopsy tissue swab samples; and
    a digital transmitting device coupled to the first and second remote applications and configured to transmit live and recorded views of the first and second set of views to an authorized third party for live and recorded viewing of the internal organs.

2. The device for self-examination of internal organs of claim 1, further comprising zoom-in and zoom-out camera controls coupled to the proximal end of the instrument to capture close-up and wide angle view images.

3. The device for self-examination of internal organs of claim 1, further comprising a data collection device coupled to the instrument configured to collect from a plurality of non-contact sensors coupled to the instrument sensor detection and measurements of pelvic and reproductive organs and tissues.

4. The device for self-examination of internal organs of claim 1, further comprising a digital pressure sensor coupled to the instrument configured to measure pressures of tissues and organs that may indicate pelvic organ prolapse.

5. The device for self-examination of internal organs of claim 1, wherein the mobile device is further configured to include a video conference module activated during a live video conference to display the pelvic images transmitted from the instrument.

6. The device for self-examination of internal organs of claim 1, wherein the light source includes lights including LED lights configured to adjust the lighting levels for camera captured images.

7. The device for self-examination of internal organs of claim 1, further comprising an infrared thermometer heat detection sensor configured to capture colorized images showing temperature variations.

8. A device for self-examination of internal organs, comprising:
    an enclosed camera having an internal gimbal and coupled to a light source and configured to capture views of the internal organs;
    wherein the enclosed camera is further configured to turn on only when the device detects it's inserted into a vagina;
    a first remote application operating on a first remote mobile device of a first user and wirelessly coupled to the enclosed camera, the internal gimbal and the light source and configured to allow the first user to display the captured views in real-time and remotely operate and control the enclosed camera and the light source and manipulate the internal gimbal to show a first set of views of the internal organs;
    a second remote application operating on a second remote mobile device of a second user and wirelessly coupled to the first remote application, wherein the second remote application is configured to allow the second remote user to remotely control the light sources and articulate and manipulate the internal gimbal independently from the first user to show a second set of views of the internal organs while the first user is communicating with the second user, wherein the second set of views are displayed to the first user via the first remote application and to the second user via the second remote application;
    a swab device removably coupled to the device and wirelessly coupled to the first and second remote applications and configured to allow the second user to remotely initiate collection of internal pelvic cavity of pelvic cytology fluid and non-biopsy tissue swab samples; and
    a digital transmitting device coupled to the first and second remote applications and configured to transmit live and recorded views of the first and second set of views to an authorized third party for live and recorded viewing of the internal organs.

9. The device for self-examination of internal organs of claim 8, wherein the swab device is inserted and maneuvered by the first user from a distal end handle coupled to an extension wherein the swab device is coupled to the extension at a proximal end to collect a cervical sample for clinical analysis.

10. The device for self-examination of internal organs of claim 8, wherein the device is configured to use for at least Pap Smear tests and sexually transmitted diseases diagnosis.

11. The device for self-examination of internal organs of claim 8, further comprising zoom-in and zoom-out camera controls coupled to the proximal end of the instrument to capture close-up and wide angle view images.

12. The device for self-examination of internal organs of claim 8, further comprising a data collection device coupled to the instrument configured to collect from a plurality of non-contact sensors coupled to the instrument sensor detection and measurements of pelvic and reproductive organs and tissues.

13. The device for self-examination of internal organs of claim 8, further comprising a digital pressure sensor coupled to the instrument configured to measure pressures of tissues and organs that may indicate pelvic organ prolapse.

14. The device for self-examination of internal organs of claim 8, wherein the mobile device is further configured to include a video conference module activated during a live video conference to display the pelvic images transmitted from the instrument.

15. A device for self-examination of internal organs, comprising:
an enclosed camera having an internal gimbal and coupled to a light source and configured to capture views of the internal organs;
a first remote application operating on a first remote mobile device of a first user and wirelessly coupled to the enclosed camera, the internal gimbal and the light source and configured to allow the first user to display the captured views in real-time and remotely operate and control the enclosed camera and the light source and manipulate the internal gimbal to show a first set of views of the internal organs;
a second remote application operating on a second remote mobile device of a second user and wirelessly coupled to the first remote application, wherein the second remote application is configured to allow the second remote user to remotely control the light sources and articulate and manipulate the internal gimbal independently from the first user to show a second set of views of the internal organs while the first user is communicating with the second user, wherein the second set of views are displayed to the first user via the first remote application and to the second user via the second remote application;
a swab device removably coupled to the device and wirelessly coupled to the first and second remote applications and configured to allow the second user to remotely initiate collection of internal pelvic cavity of pelvic cytology fluid and non-biopsy tissue swab samples;
a digital transmitting device coupled to the first and second remote applications and configured to transmit live and recorded views of the first and second set of views to an authorized third party for live and recorded viewing of the internal organs; and
a voice to text device and a language translation device coupled to the first and second remote applications and configured to convert voice conversation to text and foreign language translations of the text during a video conference transmission of the pelvic images and videos and stored data.

16. The device for self-examination of internal organs of claim 15, wherein the swab device is inserted and maneuvered by the first user from a distal end handle coupled to an extension wherein the swab device is coupled to the extension at a proximal end to collect a cervical sample for clinical analysis.

17. The device for self-examination of internal organs of claim 15, further comprising a measurement sensor device having remote controls on the mobile app coupled to the instrument configured to measure distances and sizes of openings during dilation in latent/early labor.

18. The device for self-examination of internal organs of claim 15, further comprising an infrared thermometer heat detection sensor configured to capture colorized images showing temperature variations.

19. The device for self-examination of internal organs of claim 15, wherein the device is configured to use for at least Pap Smear tests and sexually transmitted diseases diagnosis.

20. The device for self-examination of internal organs of claim 15, further comprising a digital pressure sensor coupled to the instrument configured to measure pressures of tissues and organs that may indicate pelvic organ prolapse.

* * * * *